(12) United States Patent
Lett

(10) Patent No.: US 6,457,826 B1
(45) Date of Patent: Oct. 1, 2002

(54) MULTIFOCAL ASPHERIC LENS

(76) Inventor: John B. W. Lett, 4993 Lantana Dr., San Diego, CA (US) 92105

( * ) Notice: Subject to any disclaimer, the term of this patent is extended or adjusted under 35 U.S.C. 154(b) by 0 days.

(21) Appl. No.: 09/369,680

(22) Filed: Aug. 5, 1999

Related U.S. Application Data
(60) Provisional application No. 60/095,601, filed on Aug. 6, 1998.

(51) Int. Cl.[7] .............................. G02C 7/04; A61F 2/16
(52) U.S. Cl. ...................... 351/161; 351/177; 623/6.28
(58) Field of Search .................... 351/160 R, 160 H, 351/161, 162, 177; 623/6.23, 6.24, 6.27, 6.28

(56) References Cited

U.S. PATENT DOCUMENTS

| | | |
|---|---|---|
| 1,955,047 A | 4/1934 | Beach |
| 2,405,989 A | 8/1946 | Beach |
| 3,004,470 A | 10/1961 | Rühle |
| 3,037,425 A | 6/1962 | DeCarle |
| RE25,286 E | 11/1962 | DeCarle |
| 3,279,878 A | 10/1966 | Long |
| 3,298,771 A | 1/1967 | Ratliff, Jr. |
| 3,472,581 A | 10/1969 | Bronstein |
| 3,482,906 A | 12/1969 | Volk |
| 3,614,218 A | 10/1971 | Bronstein |
| 3,662,040 A | 5/1972 | Urbach et al. |
| 3,726,587 A | 4/1973 | Kendall |
| 3,794,414 A | 2/1974 | Wesley |
| RE29,229 E | 5/1977 | Girard et al. |
| 4,055,378 A | 10/1977 | Feneberg et al. |
| 4,073,579 A | 2/1978 | Deeg et al. |
| 4,162,122 A | 7/1979 | Cohen |
| 4,199,231 A | 4/1980 | Evans |
| 4,210,391 A | 7/1980 | Cohen |
| 4,302,081 A | 11/1981 | Tsuetaki |
| 4,338,005 A | 7/1982 | Cohen |

(List continued on next page.)

FOREIGN PATENT DOCUMENTS

| | | |
|---|---|---|
| DE | 939016 | 10/1963 |
| DE | 1 199 019 | 8/1965 |
| DE | 32 22 099 A1 | 12/1983 |
| EP | 1 138 394 A2 | 4/1985 |
| EP | 0 140 063 A1 | 8/1985 |
| EP | 0 201 231 A2 | 12/1986 |
| FR | 1557212 | 2/1969 |

(List continued on next page.)

OTHER PUBLICATIONS

International Preliminary Examination Report, dated Dec. 7, 2000, for corresponding application PCT/US99/17390.

International Search Report, dated Nov. 18, 1999, for corresponding application PCT/US99/17390.

(List continued on next page.)

*Primary Examiner*—Scott J. Sugarman
(74) *Attorney, Agent, or Firm*—Brinks Hofer Gilson & Lione

(57) ABSTRACT

The present invention provides a lens having a plurality of vision areas. The plurality of areas including a first vision area, a second vision area surrounding the first vision area, and a third vision area surrounding the second vision area. The first vision area having a first power, the second vision area having a range of powers, and the third vision area having a second power distinct from the first power. One of the first, second and third vision areas having an aspheric surface designed to provide a monotonic gradient in power and the other areas having either spherical surfaces to provide single power values or aspheric surfaces designed to correct optical aberrations within these single power areas.

76 Claims, 10 Drawing Sheets

U.S. PATENT DOCUMENTS

| | | |
|---|---|---|
| 4,340,283 A | 7/1982 | Cohen |
| 4,418,991 A | 12/1983 | Breger |
| 4,525,043 A | 6/1985 | Bronstein |
| 4,549,794 A | 10/1985 | Loshaek et al. |
| 4,573,775 A | 3/1986 | Bayshore |
| 4,580,882 A | 4/1986 | Nuchman et al. |
| 4,593,981 A | 6/1986 | Scilipoti |
| 4,614,413 A | 9/1986 | Obssuth |
| 4,636,049 A | 1/1987 | Blaker |
| 4,636,211 A | 1/1987 | Nielsen et al. |
| 4,637,697 A | 1/1987 | Freeman |
| 4,693,572 A | 9/1987 | Tsuetaki et al. |
| 4,702,573 A | 10/1987 | Morstad |
| 4,704,016 A | 11/1987 | DeCarle |
| 4,728,182 A | 3/1988 | Kelman |
| 4,752,123 A | 6/1988 | Blaker |
| 4,759,763 A | 7/1988 | Bissonette et al. |
| 4,813,777 A | 3/1989 | Rainville et al. |
| 4,813,955 A | 3/1989 | Achatz et al. |
| 4,861,152 A | 8/1989 | Vinzia et al. |
| 4,869,587 A | 9/1989 | Breger |
| 4,874,234 A | 10/1989 | Wichterle |
| 4,890,912 A | 1/1990 | Visser |
| 4,890,913 A | 1/1990 | DeCarle |
| 4,898,461 A | 2/1990 | Portney |
| 4,932,970 A | 6/1990 | Portney |
| 4,936,672 A | 6/1990 | Capez |
| 4,938,583 A | 7/1990 | Miller |
| 4,950,057 A | 8/1990 | Shirayanagi |
| 4,971,432 A | 11/1990 | Koeniger |
| 4,976,534 A | 12/1990 | Miege et al. |
| 4,995,715 A | 2/1991 | Cohen |
| 5,002,382 A | 3/1991 | Seidner |
| 5,024,517 A | 6/1991 | Seidner |
| 5,071,244 A | 12/1991 | Ross |
| 5,076,683 A | 12/1991 | Glick |
| 5,080,472 A | 1/1992 | Gupta |
| 5,106,180 A | 4/1992 | Marie et al. |
| 5,125,729 A | 6/1992 | Mercyre |
| 5,129,718 A | 7/1992 | Futhey et al. |
| 5,139,325 A | 8/1992 | Oksman et al. |
| 5,141,301 A | 8/1992 | Morstad |
| 5,158,572 A | 10/1992 | Nielsen |
| 5,166,711 A | 11/1992 | Portney |
| 5,166,712 A | 11/1992 | Portney |
| 5,170,192 A | 12/1992 | Pettigrew et al. |
| 5,181,053 A | 1/1993 | Brown |
| 5,198,844 A | 3/1993 | Roffman et al. |
| 5,225,858 A | 7/1993 | Portney |
| 5,270,744 A | 12/1993 | Portney |
| 5,278,592 A | 1/1994 | Marie et al. |
| 5,296,880 A | 3/1994 | Webb |
| 5,302,978 A | 4/1994 | Evans et al. ............... 351/162 |
| 5,326,348 A | 7/1994 | Nordan |
| 5,344,447 A | 9/1994 | Swanson |
| 5,349,394 A | 9/1994 | Freeman et al. |
| 5,395,356 A | 3/1995 | King et al. |
| 5,404,183 A | 4/1995 | Seidner |
| 5,406,341 A | 4/1995 | Blum et al. |
| 5,408,281 A | 4/1995 | Zhang |
| 5,422,687 A | 6/1995 | Tanaka et al. |
| 5,430,504 A | 7/1995 | Muckenhirn et al. |
| 5,436,678 A | 7/1995 | Carroll |
| 5,483,304 A | 1/1996 | Porat |
| 5,485,228 A | 1/1996 | Roffman et al. |
| 5,493,350 A | 2/1996 | Seidner |
| 5,500,024 A | 3/1996 | Hung et al. ............... 8/509 |
| 5,517,260 A | 5/1996 | Glady et al. ............... 351/161 |
| 5,521,656 A | 5/1996 | Portney |
| 5,526,071 A | 6/1996 | Seidner et al. |
| 5,528,321 A | 6/1996 | Blum et al. |
| 5,530,491 A | 6/1996 | Baude et al. |
| 5,532,768 A | 7/1996 | Onogi et al. |
| 5,541,678 A | 7/1996 | Awanohara et al. |
| 5,574,518 A | 11/1996 | Mercure |
| 5,608,471 A | 3/1997 | Miller |
| 5,619,289 A | 4/1997 | Seidner et al. |
| 5,650,838 A | 7/1997 | Roffman et al. |
| 5,652,638 A | 7/1997 | Roffman et al. |
| 5,657,108 A | 8/1997 | Portney |
| 5,682,223 A | 10/1997 | Menezes et al. |
| 5,684,560 A | 11/1997 | Roffman et al. |
| 5,702,440 A | 12/1997 | Portney |
| 5,715,031 A | 2/1998 | Roffman et al. |
| 5,724,120 A | 3/1998 | Svochak et al. |
| 5,754,270 A | 5/1998 | Rehse et al. |
| 5,771,088 A | 6/1998 | Perrott |
| 5,796,462 A | 8/1998 | Roffman et al. |
| 5,798,817 A | 8/1998 | DeCarle |
| 5,805,260 A | 9/1998 | Roffman et al. |
| 5,812,237 A | 9/1998 | Roddy |
| 5,815,236 A | 9/1998 | Vayntraub |
| 5,815,237 A | 9/1998 | Vayntraub |
| 5,827,264 A | 10/1998 | Hohla |
| 5,835,187 A | 11/1998 | Martin |
| 5,847,802 A | 12/1998 | Menezes et al. |
| 5,864,379 A | 1/1999 | Dunn |
| 5,891,132 A | 4/1999 | Hohla |
| 5,935,140 A | 8/1999 | Buratto |
| 6,109,749 A | 8/2000 | Bernstein ............... 351/161 |

FOREIGN PATENT DOCUMENTS

| | | |
|---|---|---|
| GB | 2 086 605 A | 5/1982 |
| GB | 2 129 155 A | 5/1984 |
| JP | 1-319729 | 12/1989 |
| JP | 2-79016 | 3/1990 |
| JP | 2-217818 | 8/1990 |
| JP | 2-281229 | 11/1990 |
| JP | 5-181096 | 7/1993 |
| WO | WO 86/03961 | 7/1986 |
| WO | WO 87/00299 | 1/1987 |
| WO | WP 97/12272 | 4/1997 |
| WO | WO 98/18522 | 5/1998 |
| WO | WO 99/07440 | 2/1999 |
| WO | WO 99/44492 | 9/1999 |

OTHER PUBLICATIONS

Bier, N., "Prescribing for Presbyopia with Contact Lenses", *Opthalmic Optician*, vol. 5, No. 9, pp. 439–442 and 447–454, May 1, 1965.

Bronstein, L., "Reverse Centrad Bifocal Contact Lenses," *Optometric Weekly*, vol. 59, No. 25, pp. 45–48, Jun. 20, 1968.

Evans, T., et al., "A front aspheric hydrogel contact lens for the correction of presbyopia and astigma," Reprinted from *Optometry Today*, Nov. 5, 1988.

Ghorinley, R., "The Sunsoft Multifocal—A New Bifocal Contact Lens," ICLC, vol. 23, Mar./Apr. 1996.

Norman, C., et al., "A Soft Approach to Presbyopia," *Spectrum*, pp. 27–30, Aug. 1995.

Norman, C., et al., "Stressing Success with Your Presbyopic Contact Lens Patients," *Spectrum*, pp. 29–36, May 1995.

Pence, N., "Strategies For Success With Presbyopes," *Spectrum*, May 1994.

Wesley, N., "Analysis of Biofocal Contact Lenses," pp. 926–931, *Am. J. Optometry and Arch. Am. Ac. Optometry*, Nov. 1971.

Wu, Corrina, "Contacts for aging baby boomers' eyes?", *Science News*, vol. 150, p. 159, Sep. 7, 1996.

MULTIFOCAL ASPHERIC LENS

REFERENCE TO EARLIER FILED APPLICATION

This application claims the benefit of the filing date pursuant to 35 U.S.C. §119(e) of Provisional Application Serial No. 60/095,601, filed Aug. 6, 1998, the disclosure of which is hereby incorporated by reference.

BACKGROUND OF THE INVENTION

Simultaneous vision refers to the class of bifocal contact lenses in which optical power for distance vision and near vision are positioned simultaneously within the pupil area of a user's eye. The conventional clinical understanding for simultaneous vision is that a bifocal lens projects both distance and near images simultaneously onto the retina. Depending on the viewing distance of the object of regard, one of the images is in focus, and the other image is out of focus. It is believed that the brain is able to disregard the irrelevant out-of-focus image and to process only the relevant in-focus image. Therefore, whether an object is at distance or near locations, the lens is still able to provide levels of vision that may be acceptable to many patients.

There have been attempts to provide a simultaneous vision contact lens in the past. One type of simultaneous vision lens is the concentric zone bifocal lens in which the distance and near powers form two concentric optical zones. These lenses have included center distance or center near configurations. The dimensions of the two zones are chosen such that approximately equal areas of distance and near power are provided within the pupil area of the eye. This lens includes the advantage of providing the user with two relatively large optical areas on the lens. However, because the dimensions of a user's pupil vary from user to user and in response to ambient light levels, the relative areas of distance and near power can deviate significantly such that near vision or distance vision may be favored at the expense of the other. Since this dependence on pupil size is not under the conscious control of the user, this distance or near bias may not be appropriate for the vision requirements of a particular user.

To reduce this dependence on pupil size, additional concentric zones may be incorporated into the lens, see e.g., U.S. Pat. No. 4,704,016 (Cohen). The total bifocal optical zone of such a lens consists of a series of concentric annuli which must be within the pupil area of the eye and which alternately provide the distance and near power. But as the number of annuli increases, the width of each annulus must decrease if the zone (or at least a significant portion of it) is to remain within the pupil area. This can cause the optical quality of the distance and near powers to degrade because of the reduced dimension of each zone. In addition, undesirable edge effects are created by the boundaries between the various zones. This optical degradation can offset the potential advantages of reducing the dependence on pupil size by the incorporation of the multiple zones.

Another type of simultaneous vision lens includes within the bifocal optical zone the use of an aspheric surface which provides a continuous gradient of optical power over a selected range of powers. The steepness of the power gradient must be designed to provide the desired difference between the near power value and the distance power value (that is, the desired bifocal add power) within the pupil area of the eye. Therefore, the visual performance of the aspheric simultaneous lens design is limited by the same dependence on pupil size as in the concentric zone design. Moreover, by attempting to provide all power corrections over the full range of values between distance and near, the aspheric design compromises the quality of the vision provided at any one particular power value.

An example of an aspheric lens is U.S. Pat. No. 5,754,270 (Rehse et al.). The '270 patent discloses a lens having a centrally located aspherical first optical zone, a second aspherical concentric optical zone and a transition zone that provides a rapid power shift between the first zone and the second zone. This lens suffers from the disadvantage of compromising a user's visual acuity at a particular power value because it includes ranges of powers rather than zones with selected powers.

Yet another type of simultaneous vision lens is based on diffractive optics. In theory this lens provides nearly equal levels of distance and near vision with minimal dependence on pupil size, but in practice the clinical acceptance of diffractive bifocal contact lenses has been relatively low. It is not clear whether this low acceptance is primarily due to limitations in the inherent quality of diffractive optics or due to the complexity of the diffractive optical element which is quite difficult to manufacture.

To develop a better-performing design, it must first be recognized that the conventional explanation for simultaneous vision described above may be misleading. By describing simultaneous vision in terms of a near image and a distance image, the conventional theory assumes that there are two distinct retinal images which the brain can somehow distinguish and process separately. At any particular moment the eye is looking at a specific object of regard which is at a particular viewing distance. With all simultaneous vision lenses a partially degraded image of that object is projected onto the retina. The consequence of this image degradation is a loss of visual information (less signal, more noise), and the quality of the degraded image may or may not be acceptable to the patient. The clinical effects of this degradation may be measured objectively in terms of reduced visual acuity and contrast sensitivity. The subjective effects of the degradation are perceived by the patient in various ways which are collectively referred to as subjective blur. Therefore, when wearing a simultaneous vision lens, the patient may not be selecting between separate distance and near images. Rather, in the presence of subjective blur the patient may be attempting to function with the reduced level of visual information that is provided by a degraded image.

The visual system does have the ability to filter out some of the noise, and many patients demonstrate a tremendous potential to adapt to subjective blur. In some patients the adaptation is so complete that they may not report any subjective blur even though by objective measures their vision may be obviously compromised. However, the opposite situation may occur where an objective assessment indicates normal vision performance, but the patient paradoxically complains of poor vision.

Therefore, there is a need for an improved simultaneous lens design that maximizes the available visual information for objects of regard at distance and at near locations and concurrently minimizes visual disturbances.

SUMMARY OF THE INVENTION

The present invention provides an optimized lens construction that provides for the reduction of visual disturbances that result from the transitions between areas as formed in past lenses while providing an enhanced visual acuity over a range of distances. There is also a need for a lens that combines the positive features of a concentric design with the positive features of an aspheric design in a unique integrated design that minimizes the disadvantages of each.

Briefly stated, the present invention provides a lens having a plurality of vision areas. The plurality of areas including a first vision area, a second vision area surrounding the first vision area, and a third vision area surrounding the second vision area. The first vision area having a first power, the second vision area having a range of powers, and the third vision area having a second power distinct from the first power. One of the first, second and third vision areas having an aspheric surface designed to provide a monotonic gradient in power and the other areas having either spherical surfaces to provide single power values or aspheric surfaces designed to correct optical aberrations within these single power areas.

The present invention also provides a lens having a plurality of vision areas. The areas include a first vision area, a second vision area, and a third vision area. The second vision area is between the first vision area and the third vision area. The first, second and third vision areas defining a portion of a surface profile of the lens wherein the direction of concavity does not change even though the power profile may show adjoining areas of single power values and gradient power values.

The present invention is also directed to an ophthalmic kit. The kit includes a sterile packaged contact lens in a bacteriostatic solution in accordance with the present invention. The kit can include the lens secured in a vial or a blister package.

According to yet another aspect of invention, a method of using a contact lens is provided. According to a first step, a user places the contact lens over a pupil of the user's eye. The contact lens has a transition from a first vision area having a first power and a second vision area having a second power.

As used herein, the term "lens" is intended to be interpreted broadly to include a wide variety of lenses including contact lenses and intraocular lenses.

As also used herein, the term "power" is intended to be interpreted broadly to include a single power or an average power.

As further used herein, the term "range of powers" is intended to be interpreted broadly to include a series of substantially continuous or non-continuous powers.

As used herein, the term "area" is intended to be interpreted broadly to include zones or regions.

As used herein, the term "vision area" is intended to include area that contributes to the vision of a user.

The present invention, together with attendant objects and advantages, will be best understood with reference to the detailed description below in connection with the attached drawings.

DETAILED DESCRIPTION OF THE DRAWINGS AND THE PREFERRED EMBODIMENTS

Figure 1:
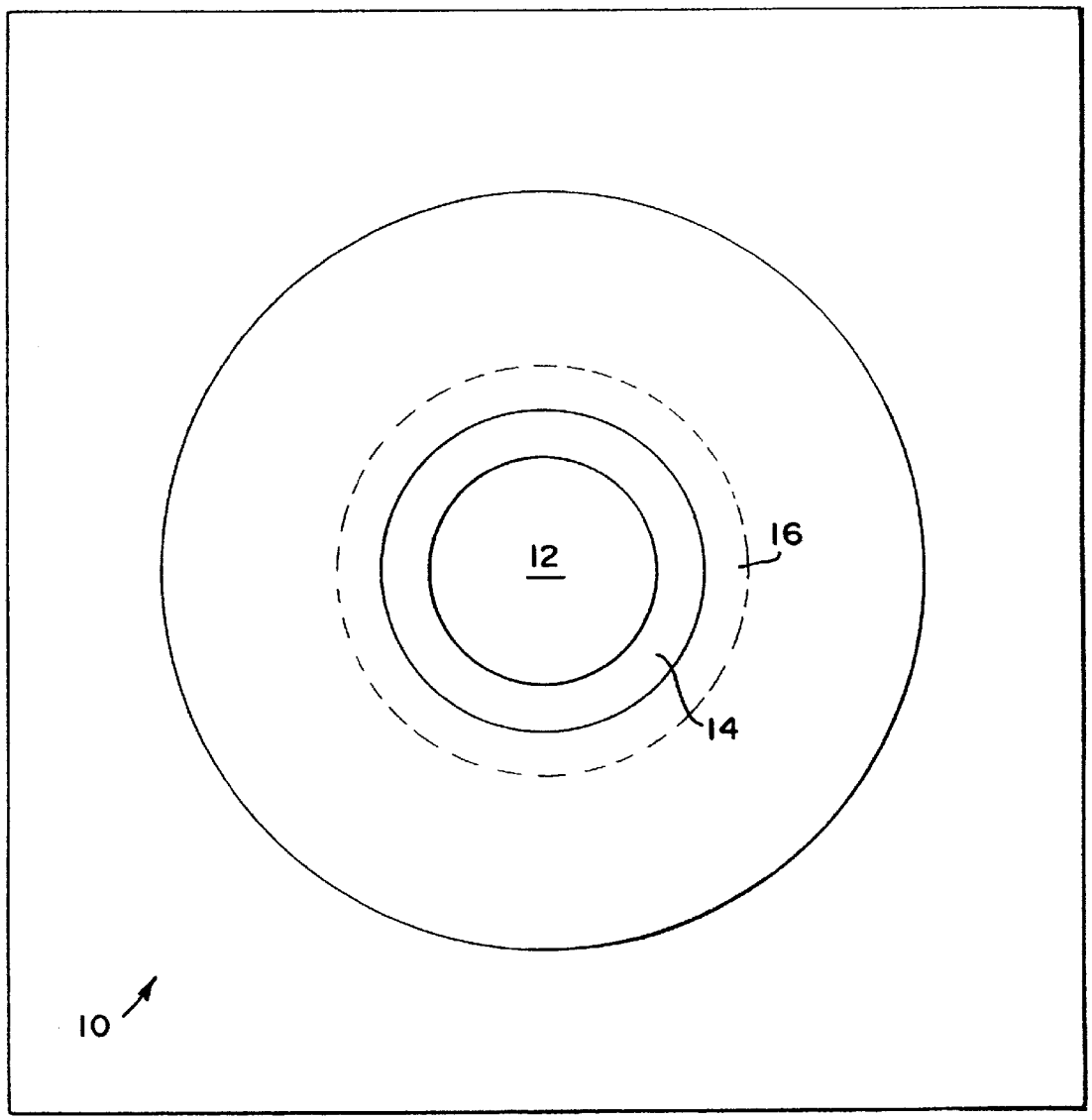
FIG. 1 is a front view of the optical portion of a contact lens constructed in accordance with one preferred embodiment of the present invention.
Figure 3:
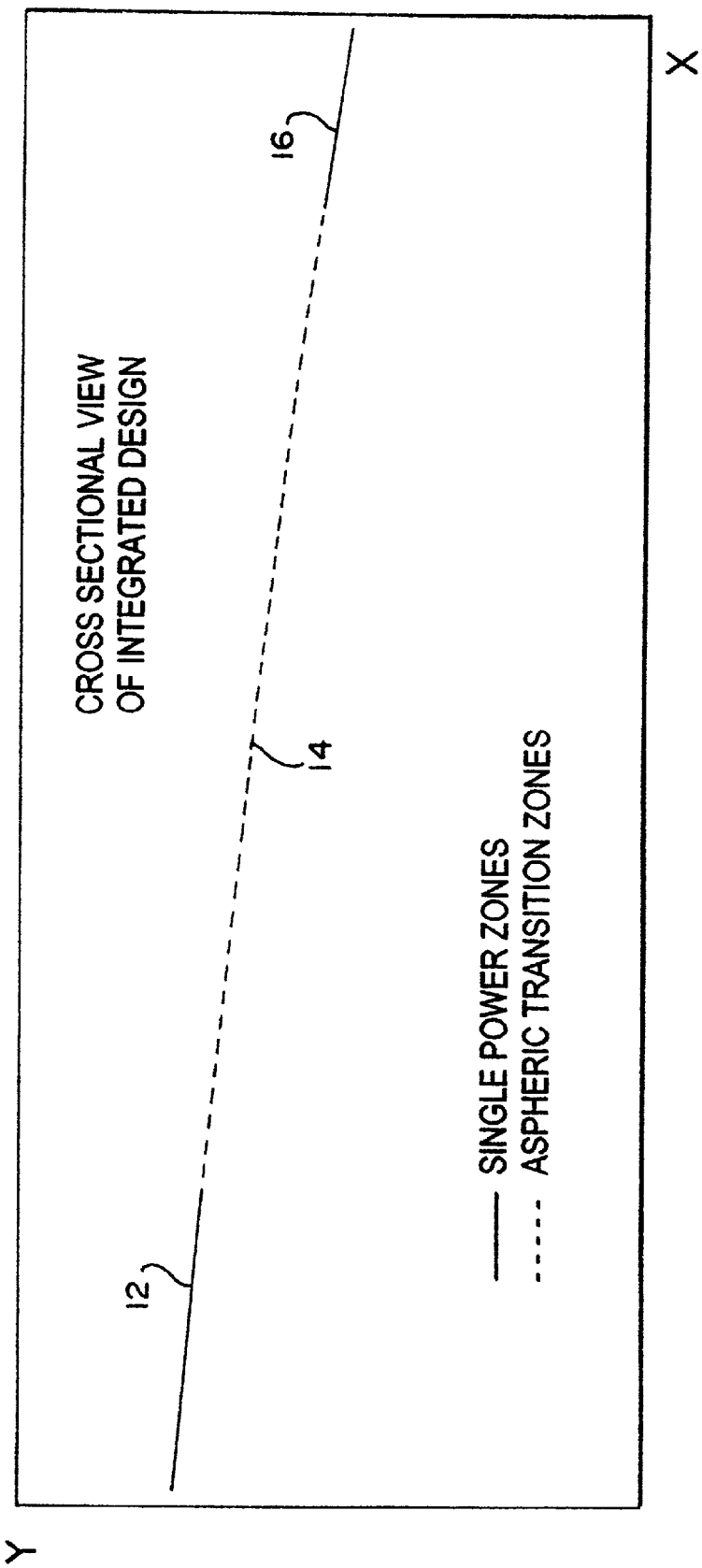
FIG. 3 is a graph that illustrates the cross-section of the preferred embodiment illustrated in FIG. 1.

FIG. 1 is a front view of the optical portion of one preferred embodiment of the present invention that is also represented in part by the graph shown in FIG. 3. FIG. 1 illustrates a contact lens 10 having a center near configuration. The center area 12 is a single power area that provides the desired near power. The outer area 16 is a single power area that provides the desired distance power. Intermediate area 14 is a gradient power aspheric area which provides a continuous and monotonic power change from the near power of area 12 to the distance power of area 16. While the center area 12 and outer area 16 are single power areas in the preferred embodiment, it should be recognized that each of these areas could also be formed from a plurality of areas having multiple powers. The dashed circle within the area 16 represents the dimensions of a typical pupil size.

The intermediate area 14 acts as an area of extended depth of focus. As such, the intermediate area 14 contributes to vision over a range of object distance including that for distance vision, near vision, and intermediate distance vision. When the object of regard is at a near position, center area 12 and intermediate area 14 in combination (approximately 70% of the area of a 3.0 mm pupil or approximately 52% of the area of a 3.5 mm pupil in one of the following examples) contribute to near vision. When the object of regard is at a distance position, intermediate area 14 and outer area 16 in combination (approximately 61% of the area of a 3.0 mm pupil or approximately 72% of the area of a 3.5 mm pupil in one of the following examples) contribute to distance vision. At intermediate distances, the intermediate area 14 provides a useful level of intermediate distance vision over approximately 32% of the area of a 3.0 mm pupil or approximately 24% of the area of a 3.5 mm pupil.

The dimensions of the three areas must be calculated appropriately to maximize use of the pupil area for both distance and near vision and will depend on various factors such as needed power, pupil size, eye aberration and other patient and application related factors. Thus, if desired, each lens may be custom made to meet the specific power prescription and other individual characteristics of the user. In addition to the user's distance and near power prescription, factors such as pupil size, vocational requirements, and even personal habits and preferences can be considered to produce a custom designed lens; i.e., a lens having optical areas, power values, and dimensions specifically selected to suit the needs of a particular user. Alternatively, the dimensions of the three areas may be standardized to a few choices which satisfy most requirements of an average user population but which are also compatible with the economy of scale derived from volume manufacturing. A toric surface may also be used with the lens to correct an astigmatism. The toric surface would be used on the side opposite the areas 12, 14, 16.

In one embodiment, the diameter for each area and the percentage of pupil area for typical pupil sizes are listed as follows:

TABLE 1

| Area | Diam | Power | % Area within 3.0 mm pupil | % Area within 3.5 mm pupil | % Area within 4.0 mm pupil | % Area within 4.5 mm pupil | % Area within 5.0 mm pupil |
|---|---|---|---|---|---|---|---|
| Area 12 | 1.86 mm | Near | 38% | 28% | 22% | 17% | 14% |
| Area 14 | 2.52 mm | Gradient | 32% | 24% | 18% | 14% | 12% |
| Area 16 | 8.00 mm | Distance | 29% | 48% | 60% | 69% | 75% |

In the most preferred embodiment, the diameter for each area and the percentage of pupil area for typical pupil sizes are listed as follows:

TABLE 2

| Area | Diam | Power | % Area within 3.0 mm pupil | % Area within 3.5 mm pupil | % Area within 4.0 mm pupil | % Area within 4.5 mm pupil | % Area within 5.0 mm pupil |
|---|---|---|---|---|---|---|---|
| Area 12 | 1.83 mm | Near | 37% | 27% | 21% | 17% | 13% |
| Area 14 | 2.46 mm | Gradient | 30% | 22% | 17% | 13% | 11% |
| Area 16 | 8.00 mm | Distance | 33% | 51% | 62% | 70% | 76% |

While the preferred embodiments are illustrated in Tables 1–2, the center area 12 can have a range of between 1.0 and 3.8 mm, or more preferably between 1.2 mm and 2.1 mm, and most preferably between 1.5 mm and 1.9 mm. The intermediate area 14 can have a minimum diameter of 1.2 mm and a maximum diameter of 4.8 mm, or more preferably between an inner diameter within the range of 1.2 mm and 2.1 mm and an outer diameter between 2.3 mm and 3.0 mm. The outer area 16 can have a minimum diameter of 2.0 mm and a maximum diameter of 10.0 mm or more preferably an inner diameter between 2.3 mm and 3.0 mm and an outer diameter between 4.0 mm and 9.0 mm.

The lens can readily be designed to have bifocal Add powers of any desired value. In normal clinical practice, the most commonly prescribed Add powers are in the range of +0.75 D to +2.50 D, but Add powers beyond this range are prescribed occasionally. The radii of curvature for the center area 12 and the outer area 16 are then determined from the prescribed distance power and Add power from the standard optical formulas which are used routinely by those skilled in the art. The variables which specify the aspheric area of the present invention are then determined using the methods described in detail below. Listed in the tables below are the resulting specifications for a sample range of distance powers in a lens with a +1.50 D Add power with the zone dimensions given above in Tables 1–2. In the tables $r_1$, $r_2$, and $r_3$ are variables which describe the radii of curvature of the central, intermediate, and outer areas, $p_2$ is a variable which describes the asphericity of the intermediate area, and $\epsilon_2$ and $\epsilon_3$ are position variables for the intermediate and outer areas. All these variables are more fully explained below when the formal mathematical descriptions of these respective surfaces are developed. It is assumed in these examples that the multiple optical areas are on the anterior surface of the contact lens, but if desired each example may be computed for its equivalent posterior surface configuration.

Radius Posterior Surface: 8.30 mm

Center Thickness: 0.08 mm

Refractive Index: 1.412

Bifocal Add Power: +1.50 D

TABLE 3

(For Embodiment of Table 1)

| Distance Power | Central Area 12 | Aspheric Area 14 | | | Outer Area 16 | |
|---|---|---|---|---|---|---|
| | $r_1$ | $r_2$ | $p_2$ | $\epsilon_2$ | $r_3$ | $\epsilon_3$ |
| −5.00 | 8.953 | 8.579 | −6.5612 | −0.0010 | 9.253 | 0.0022 |
| −4.00 | 8.764 | 8.406 | −6.0829 | −0.0010 | 9.051 | 0.0022 |
| −3.00 | 8.582 | 8.240 | −5.6441 | −0.0010 | 8.857 | 0.0022 |
| −2.00 | 8.408 | 8.080 | −5.2409 | −0.0010 | 8.672 | 0.0022 |
| −1.00 | 8.241 | 7.926 | −4.8697 | −0.0010 | 8.494 | 0.0022 |

TABLE 4

(For Embodiment of Table 2)

| Distance Power | Central Area 12 | Aspheric Area 14 | | | Outer Area 16 | |
|---|---|---|---|---|---|---|
| | $r_1$ | $r_2$ | $p_2$ | $\epsilon_2$ | $r_3$ | $\epsilon_3$ |
| −5.00 | 8.953 | 8.562 | −7.1303 | −0.0011 | 9.253 | 0.0021 |
| −4.00 | 8.764 | 8.390 | −6.6160 | −0.0011 | 9.051 | 0.0021 |
| −3.00 | 8.582 | 8.224 | −6.1442 | −0.0011 | 8.857 | 0.0021 |
| −2.00 | 8.408 | 8.065 | −5.7106 | −0.0010 | 8.672 | 0.0021 |
| −1.00 | 8.241 | 7.912 | −5.3115 | −0.0010 | 8.494 | 0.0022 |

Figure 2:
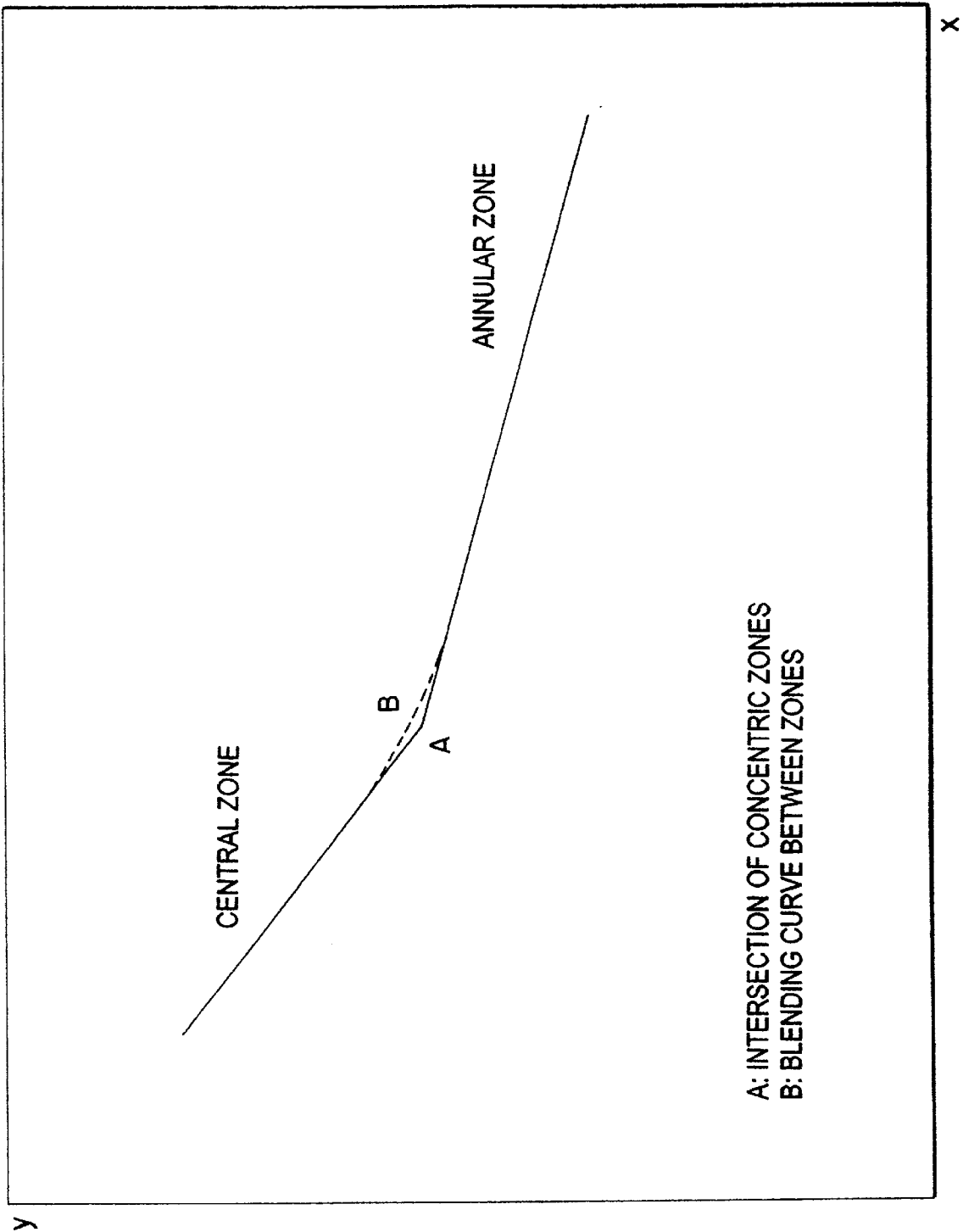
FIG. 2 is a graph that illustrates a cross-section of a prior art lens.

The transition between the center area 12 and the intermediate area 14, as well as the transition between the intermediate area 14 and the outer area 16, has a significant impact on visual acuity which is an improvement over the prior art. FIG. 2 illustrates the appearance in cross section of a prior art concentric two-area bifocal lens (the curves are exaggerated to make the features of the surface profile visible in the figure). At the intersection (at point A in FIG. 2) of the two concentric areas, there is a sharp corner in the surface profile, and there is a discontinuity in the local tangent to the surface profile at this sharp corner. Thus, the local tangent to the surface profile approaches different limiting values as the intersection is approached from either side of the corner. The presence of the sharp corner produces undesirable edge effects due to diffraction and also due to the prismatic difference that is induced between off-axis rays incident on either side of the corner. In spectacle bifocal lenses this induced prismatic difference is known as "bifocal jump," and most spectacle bifocal lenses are specifically designed to reduce this disturbing visual effect.

The sharp corner at A in FIG. 2 may be rounded by a blending curve connecting the two areas (the dashed curve B in FIG. 2). Such a blend curve can eliminate the discontinuity in the local tangent to the surface profile and may, for example, be created by a polishing or buffing operation on the original unblended surface. However, merely rounding a sharp corner does not completely eliminate the corner nor its effects. As shown in FIG. 2, the surface profile in the region of the original concentric areas is concave downward in the figure, but the region of the blend curve B is concave upwards in the figure. Even though there is no discontinuity in the tangent, the slope is sometimes increasing in value and sometimes decreasing in value. This means that the second derivative to the surface profile changes sign at either side of the rounded corner. The potential for a disturbing edge effect is still present in such a blended profile. The transition of the present invention significantly avoids these disturbing effects.

FIG. 3 partially illustrates the embodiment of FIG. 1 when viewed in cross-section. The surface profile of the intermediate aspheric area 14 is indicated in FIG. 3 by a dashed line to make it distinguishable from the center area 12 and the outer area 16, which are indicated by solid lines. There are no visible physical demarcations at the boundaries of the intermediate area 14 with either the center area 12 or the outer area 16 of the preferred embodiment. Thus, the profile is smooth, continuous, without sharp or rounded corners, and always concave downward for the particular configuration. Since the intermediate area 14 between the center area 12 and the outer area 16 is completely seamless, there are no sharp boundaries to cause undesirable edge disturbances such as the bifocal jump effect.

Each of the surface areas or zones of the present invention is a surface of revolution. As such the surface of each zone may be specified mathematically in two dimensions in terms of its cross section. The full three dimensional surface is then generated by rotating the cross section about an axis of revolution. In the simplest form of the present invention, this axis of revolution is also the optical axis of the contact lens, and the geometrical center of the contact lens lies on this axis. However, it may also be appropriate to decenter the optical areas of the contact lens from the contact lens geometrical center in order to achieve a more favorable positioning of the optics with respect to the eye. For example, if the average position of the contact lens is not centered with respect to the eye, it can be desirable to decenter the optical areas such that they are centered with respect to the eye rather than to the contact lens. Furthermore, it is known that the eye itself is not a centered system. Thus, the pupil is usually not centered with respect to the visible iris, and the visual axis of the eye is usually not centered with respect to the pupil. One can compensate for all these various alignment deviations by decentering the optics of the contact lens such that the final position of the optical areas is centered with respect to the pupil or to the visual axis of the eye. To maintain this desired alignment of the optical areas with respect to the eye, the contact lens must also incorporate an appropriate system for ballasting the lens such as commonly found in toric contact lenses. For example, a prism ballast system may be used to maintain the proper orientation of the contact lens on the eye. However, no such ballasting system is required for the case when the geometrical center of the lens lies on the optical axis.

The cross sectional surface profile of an aspheric surface of revolution may conveniently be described in terms of a conic section. If the cross section of the surface of revolution is not a true conic section, any small region of the surface profile may still be closely approximated by a portion of a conic section.

One form of the equation for a conic section in given in Eq. (1) where r is the radius of curvature at the apex of the surface (the apical radius), y is distance of a point on the surface from the axis of the conic section, and x is the distance of the surface point from the apex in the direction of the axis. In contact lens technology the distance x is commonly referred to as the sagittal distance or as the sagittal depth, and 2y is the chord diameter (y is the half chord diameter) for the sagittal distance x. Eq. (1) is convenient because it may be used to describe both spherical and aspherical surfaces.

$$y^2 = 2rx - px^2 \qquad \text{Eq. (1)}$$

$$p = 1 - e^2 \text{ for a flattening surface} \qquad \text{Eq. (2)}$$

$$p = 1/(1-e^2) \text{ for a steepening surface} \qquad \text{Eq. (3)}$$

$$p = 1 + k \text{ or } k = p - 1 \qquad \text{Eq. (4)}$$

The variable p is a quantity that describes the asphericity of the surface and is related to the familiar eccentricity e of the conic section by Eq. (2) or by Eq. (3). Eq. (2) applies if the surface curvature becomes flatter as a point on the surface moves away from the apex position, and Eq. (3) applies if the surface curvature becomes steeper as the point moves away from the apex position. The use of the related variable k=p−1 in Eq. (4) as the asphericity variable is also appropriate.

The relationship between these asphericity variables and the common types of surfaces of revolution is summarized in the table below.

TABLE 5

| Type | Conic Section | Surface | p | e | k |
|---|---|---|---|---|---|
| Flattening | Circle | Sphere | p = 1 | e = 0 | k = 0 |
| | Ellipse | Ellipsoid | 0 < p < 1 | 0 < e < 1 | −1 < k < 0 |
| | Parabola | Paraboloid | p = 0 | e = 1 | k = −1 |
| | Hyperbola | Hyperboloid | p < 0 | 1 < e | k < −1 |
| Steepening | Ellipse | Ellipsoid | 1 < p | 0 < e < 1 | 0 < k |

Thus, with the appropriate selection of the asphericity variable p, Eq. (2) may be used to describe both spherical and aspherical surfaces.

Since the present invention provides a contact lens having a plurality of areas, Eq. (1) may be elaborated as in Eq. (5) where the index i is used to denote the equation describing the $i^{th}$ surface area. Thus, i=1 denotes the first surface area, i=2 denotes the second area, and so on.

$$y^2 = 2r_i x - p_i x^2; \ i=1, 2, 3, \ldots \qquad \text{Eq.(5)}$$

Eq. (5) describes a surface in which the apex of the surface is located at the origin of the coordinate system. To allow for the fact that the apices of the different surfaces are not all be at the origin, Eq. (5) must be further generalized as in Eq. (6) where $\epsilon_i$ and $\eta_i$ are respectively the x and y coordinates of the apex of the surface.

$$(y - \eta_i)^2 = 2r_i(x - \epsilon_i) - p_i(x - \epsilon_i)^2 \qquad \text{Eq. (6)}$$

The inverse relationship for Eq. (6) is given in Eq. (7). This equation provides a convenient expression for the sagittal depth of the surface as a function of the (half) chord diameter.

$$(x - \varepsilon_i) = \frac{(y - \eta_i)^2 / r_i}{1 + \sqrt{1 - p_i(y - \eta_i)^2 / r_i^2}} \quad \text{Eq. (7)}$$

The surfaces of the present invention are not limited to those derived from conic sections. To accommodate aspheric surfaces which depart from conic sections, Eq. (7) may be further generalized to include higher order terms as in Eq. (8). The inclusion of such higher order terms may be desirable in order to minimize or eliminate certain optical aberrations.

$$(x - \varepsilon_i) = \frac{(y - \eta_i)^2 / r_i}{1 + \sqrt{1 - p_i(y - \eta_i)^2 / r_i^2}} + a(y - \eta_i)^4 + b(y - \eta_i)^6 + \ldots \quad \text{Eq. (8)}$$

For simplicity in the mathematical development, these higher order terms are not included in the description that follows, although they may be incorporated, if desired, in alternative embodiments of the present invention. Therefore, Eq. (7) rather than Eq. (8) is used in the development below.

In a preferred embodiment of the present invention the front surface of the contact lens comprises three zones within the multifocal optical zone. Although each zone has its own characteristics and requirements, the surface which comprises the three zones may be simply described by the following equations which are derived from Eq. (6) above.

$$(y - \eta_1)^2 = 2r_1(x - \epsilon_1) - p_1(x - \epsilon_1)^2, \text{ for } Z_1 \geq 2y \geq 0 \quad \text{Eq. (9)}$$

$$(y - \eta_2)^2 = 2r_2(x - \epsilon_2) - p_2(x - \epsilon_2)^2, \text{ for } Z_2 \geq 2y \geq Z_1 \quad \text{Eq. (10)}$$

$$(y - \eta_3)^2 = 2r_3(x - \epsilon_3) - p_3(x - \epsilon_1)^2, \text{ for } Z_3 \geq 2y \geq Z_2 \quad \text{Eq. (11)}$$

In these equations $Z_1$ is the chord diameter of the central first zone, $Z_2$ is the chord diameter (the outer diameter) of the second zone, and $Z_3$ is the chord diameter of the third zone. Thus, the surface profiles of the three zones are fully defined by the above equations once specific values are assigned to the variables $r_i$, $p_i$, $\epsilon_i$, $\eta_i$, and $Z_i$ for i=1, 2, and 3.

The unique characteristics of the present invention may now be described in terms of their physical and mathematical requirements. These requirements are then used to derive the values for the variables $r_i$, $p_i$, $\epsilon_i$, $\eta_i$, and $Z_i$ which specify the preferred embodiment of the present invention.

A starting point for the specification of the preferred embodiment is the selection of the zone dimensions $Z_1$, $Z_2$, and $Z_3$. The largest zone $Z_3$ is analogous to the optical zone dimension in a conventional single vision lens. As such it is designed to be significantly larger than the average pupil diameter of the eye. Thus, a typical value for $Z_3$ is 8.0 mm. There is a great deal of latitude in the dimension, but it is normally not smaller than perhaps 6.0 mm or 6.5 mm. Also, although the theoretical upper limit for $Z_3$ is the full diameter of the lens, $Z_3$ is usually smaller than the lens diameter in order to prevent the central or peripheral areas of the lens from becoming either too thick or too thin. Therefore, in the preferred embodiment $Z_3$ is set at 8.0 mm for many low to mid-range powers, but larger or smaller values of $Z_3$ are acceptable or desirable for powers in the higher plus or higher minus range.

In the preferred embodiment the central zone 10 is a single power zone which is designed to provide the power required for near vision. In prior art lenses in which a central zone contains the near power, the dimension for $Z_1$ is chosen such that the area of the central near zone is substantially equal to 50% of the pupil area of the eye for an average pupil diameter of 3.0 mm to 3.2 mm. For example, a central zone in which $Z_1$ is equal to 2.1 mm provides a central area which is approximately 50% of the area of a 3.0 mm pupil. The rationale for this choice is that the simultaneous presence of both distance and near power areas within the pupil of the eye represents a degree of compromise to the user and that the best balance between distance and near vision requirements must be to make each power area substantially equal to 50% of the pupil area.

However, this rationale is not based on analysis of the full visual needs of the average presbyopic person. An improved multifocal lens would not only provide superior distance and near vision quality but also vision for intermediate viewing distances. Therefore, it is an object of the present invention to provide at least three optical zone areas to provide distance power, near power, and progressive power for intermediate distance vision. A natural geometrical consequence of incorporating such a third zone with progressive power and which occupies a substantial portion of the pupil area is that the central near power zone must now be limited in size to occupy substantially less than 50% of the pupil area.

Apart from the geometrical implications of incorporating at least three optical zone areas within the pupil area, it is another object of the present invention to provide an optimum configuration of zone areas such that the visual needs of an average user are satisfied over a widest range of common daily activities. To this end the size of the central near zone must be large enough to provide for comfortable reading vision. However, if the central near zone is too large, then near vision may be improved but at the expense of reducing the quality of distance vision and intermediate vision to the extent that these may be unacceptably compromised. Therefore, to achieve a full range of power requirements, it is found that the visual needs of the user are best satisfied when the area of the central near zone is substantially less than 50%.

In a preferred embodiment a dimension of $Z_1$=1.86 mm provides for a central near zone 12 which is approximately 38% of a 3.00 mm pupil diameter. For larger pupil diameters this same central near zone 12 represents a smaller portion of the pupil area. For example, the $Z_1$=1.86 mm central near zone 12 dimension which represents about 38% of the area of a 3.00 mm pupil would represent only about 28% of the area of a 3.50 mm pupil.

The annular second zone 14 is an area of gradient power and provides for intermediate distance vision. Its outer dimension $Z_2$ must be selected to provide for a useful optical area of gradient power within the pupil while still preserving the vision quality of distance vision provided by the outermost third optical area or zone.

The variables $r_i$, $p_i$, $\epsilon_i$, and $\eta_i$ for the first and third zones are relatively straightforward to specify since these are single power zones which are designed to provide the distance and near optical power requirements. In the preferred embodiment, these single power zones may be spherical or they may be aspherical for the purpose of correcting optical aberration such as the spherical aberration of the contact lens or of the eye. Because the dimensions of the zones are chosen to fit within the pupil of the eye, the relevant spherical aberration of the single power zones is relatively small. Thus, for pupil sizes under 3.6 mm, the spherical aberration within the corresponding areas of the contact lens is substantially less than about 0.25 D for most powers. Consequently, the aspherical adjustment needed to correct this level of aberration is also small. The spherical aberration of the eye varies among individuals but is usually not larger than about 0.50 D for pupils under 3.6 mm. This would require a somewhat larger aspherical adjustment, but it is still relatively small compared to that required for the multifocal power range of the contact lens.

For simplicity in the following mathematical development, the single power zones are assumed to be spherical which means that their asphericity values are given simply by $p_1=p_3=1$. Moreover, the spherical radii of curvature $r_1$ and $r_3$ for these zones are determined by the distance and near power prescription of the lens. Furthermore, the centers of curvature of these two spherical zones define the optical axis of the lens. Then by definition the apices of these spherical zones must lie on the optical axis; hence, we have that $\eta_1=\eta_3=0$.

The apex positions of the first and third surfaces along the optical axis are specified by $\epsilon_1$ and $\epsilon_3$ respectively. By convention the origin of the coordinate system may be placed without loss of generality at the apex of the surface of the central zone, $\epsilon_1=0$. The apex position of the third surface is then determined only by the value of $\epsilon_3$. The apex position $\epsilon_3$ also determines $\gamma_{13}$ which is the distance between the centers of curvature of the first and third surfaces and is given by Eq. (12).

$$\gamma_{13}=(r_1+\epsilon_3)-(r_1+\epsilon_1)=(r_3+\epsilon_3)-r_1 \quad \text{Eq. (12)}$$

In the absence of the second annular zone, the first and third spherical surfaces with the distance between centers $\gamma_{13}$ would intersect at a hypothetical zone boundary with the diameter $Z_{13}$ given by Eq. (13).

$$z_{13} = 2r_1 \sin\alpha \text{ where } \cos\alpha = \frac{r_3^2 - r_1^2 - \gamma_{13}^2}{2\gamma_{13}r_1} \quad \text{Eq. (13)}$$

$\epsilon_3$ and therefore $\gamma_{13}$ must be chosen such that $Z_{13}$ satisfies Eq. (14) below. The hypothetical intersection boundary of the first and third surfaces must lie within (and be replaced by) the surface of the second zone. Otherwise, the first and third surfaces would intersect at a boundary outside of the second zone and an additional zone would be unintentionally created.

$$Z_1 \leq Z_{13} \leq Z_2 \quad \text{Eq. (14)}$$

It might first appear that Eq. (14) permits a degree of latitude in the selection of $\epsilon_3$ such that there is a corresponding latitude in the value of $\gamma_{13}$. However, it will be seen below that the desired characteristics of the power gradient within the second zone 14 provides an additional and important constraint on $\epsilon_3$ which is not described in multifocal lenses of the prior art.

It now remains to develop values for $r_2$, $p_2$, $\epsilon_2$, and $\eta_2$ which complete the specification for the aspheric surface of the second zone. It is an integral feature of the present invention that the tangent to the lens surface is at all points continuous, in particular at the boundaries between the different areas or zones. The tangent to the surface profile for the $i^{th}$ zone is most conveniently described in terms of the first derivative $y'$. This is computed from Eq. (6) to give Eq. (15) below.

$$(y-\eta_i)' = y' = \frac{r_i - p_i(x-\epsilon_i)}{(y-\eta_i)} \quad \text{Eq. (15)}$$

Eq. (15) may also be combined with the inverse relationship given in Eq. (7) to obtain Eq. (16). This equation is convenient because it provides an expression for calculating the tangent directly from the chord diameter and does not require explicit knowledge of the sagittal depth.

$$(y-\eta_i)y' = r_i - p_i(x-\epsilon_i) = r_i - \frac{p_i(y-\eta_i)^2/r_i}{1+\sqrt{1-p_i(y-\eta_i)^2/r_i^2}} \quad \text{Eq. (16)}$$

The continuity requirements for $y$ and $y'$ are now applied in order to solve for the variables $r_2$, $p_2$, $\epsilon_2$, and $\eta_2$ which specify the aspheric surface of the second zone. For convenience, the quantities $x_1$, $y_1$, $y_1'$ and $x_3$, $y_3$, $y_3'$ are defined below. The half chord diameter is given by Eq. (17) at the boundary between the first and second zones. We then define $x_1$, $y_1$, $y_1'$ by Eq. (18) to Eq. (20).

$y=Z_1/2$ at boundary between first and second zones  Eq. (17)

Let $y_1=Z_1/2$  Eq. (18)

$x_1=x$ when $y=y_1$  Eq. (19)

$y_1'=y'$ when $y=y_1$  Eq. (20)

Similarly, the half chord diameter is given by Eq. (21) at the boundary between the second and third zones, and $x_3$, $y_3$, $y_3'$ are defined by Eqs. (22) to (24).

$y=Z_2/2$ at boundary between second and third zones  Eq. (21)

Let $y_3=Z_2/2$  Eq. (22)

$x_3=x$ when $y=y_3$  Eq. (23)

$y_3'=y'$ when $y=y_3$  Eq. (24)

In terms of the above quantities $x_1$, $y_1$, $y_1'$, $x_3$, $y_3$, and $y_3'$ the continuity feature of the present invention may be summarized concisely as four conditions or equations. From Eq. (6) we obtain Eqs. (25) and (26), and from Eq. (16) we obtain Eqs. (27) and (28).

$(y_1-\eta_2)^2=2r_2(x_1-\epsilon_2)-p_2(x_1-\epsilon_2)^2$  Eq. (25)

$(y_3-\eta_2)^2=2r_2(x_3-\epsilon_2)-p_2(x_3-\epsilon_2)^2$  Eq. (26)

$(y_1-\eta_2)y_1'=r_2-p_2(x_1-\epsilon_2)$  Eq. (27)

$(y_3-\eta_2)y_3'=r_2-p_2(x_3-\epsilon_2)$  Eq. (28)

These Eqs. (25) to (28) represent a system of four non-linear equations in the four unknowns $r_2$, $p_2$, $\epsilon_2$, and $\eta_2$. Because this system of equations is non-linear, It is convenient to step back and recast Eq. (6) for the second surface into the general quadratic expression in Eq. (29).

$Ax^2+By^2+Cxy+Dx+Ey=1$  Eq. (29)

Eq. (29) may be simplified slightly by eliminating the cross product term $Cxy$. In the general case this may always be accomplished by appropriate rotation of the coordinate system, but from the symmetry of the surface of revolution of the present invention, it may be assumed that the appropriate coordinate rotation has already been performed and therefore that $C=0$. Thus, an alternative but equivalent expression for the second surface is given by Eq. (30), and the corresponding relation for the tangent is given by Eq. (31).

$Ax^2+By^2+Dx+Ey=1$  Eq. (30)

$2Ax+2Byy'+D+Ey'=0$  Eq. (31)

The four equations equivalent to the continuity requirements of Eqs. (25) to (28) are then given by the following.

$Ax_1^2 + By_1^2 + Dx_1 + Ey_1 = 1$  Eq. (32)

$Ax_3^2 + By_3^2 + Dx_3 + Ey_3 = 1$  Eq. (33)

$2Ax_1 + 2By_1y_1' + D + Ey_1' = 0$  Eq. (34)

$2Ax_3 + 2By_3y_3' + D + Ey_3' = 0$  Eq. (35)

Eqs. (32) to (35) are a system of four equations in the four unknowns A, B, D, and E. However, a major advantage of this formulation compared to Eqs. (25) to (28) is that this is now a system of linear equations in the four unknowns and is susceptible to solution by standard methods. In particular the solution to this system may be written directly by using the method of Cramer's Rule and the appropriate 4×4 determinants. Thus, let Q denote the determinant defined below in Eq. (36).

$$Q = \begin{vmatrix} x_1^2 & y_1^2 & x_1 & y_1 \\ x_3^2 & y_3^2 & x_3 & y_3 \\ 2x_1 & 2y_1y_1' & 1 & y_1' \\ 2x_3 & 2y_3y_3' & 1 & y_3' \end{vmatrix}$$  Eq. (36)

Then by applying Cramer's Rule (and if the above determinant Q is not zero) the four unknowns A, B, D, and E are given by Eqs. (37) to (40).

$$A = Q^{-1} \cdot \begin{vmatrix} 1 & y_1^2 & x_1 & y_1 \\ 1 & y_3^2 & x_3 & y_3 \\ 0 & 2y_1y_1' & 1 & y_1' \\ 0 & 2y_3y_3' & 1 & y_3' \end{vmatrix}$$  Eq. (37)

$$B = Q^{-1} \cdot \begin{vmatrix} x_1^2 & 1 & x_1 & y_1 \\ x_3^2 & 1 & x_3 & y_3 \\ 2x_1 & 0 & 1 & y_1' \\ 2x_3 & 0 & 1 & y_3' \end{vmatrix}$$  Eq. (38)

$$D = Q^{-1} \cdot \begin{vmatrix} x_1^2 & y_1^2 & 1 & y_1 \\ x_3^2 & y_3^2 & 1 & y_3 \\ 2x_1 & 2y_1y_1' & 0 & y_1' \\ 2x_3 & 2y_3y_3' & 0 & y_3' \end{vmatrix}$$  Eq. (39)

$$E = Q^{-1} \cdot \begin{vmatrix} x_1^2 & y_1^2 & x_1 & 1 \\ x_3^2 & y_3^2 & x_3 & 1 \\ 2x_1 & 2y_1y_1' & 1 & 0 \\ 2x_3 & 2y_3y_3' & 1 & 0 \end{vmatrix}$$  Eq. (40)

When the terms in Eq. (6) are expanded and the coefficients for x, $x^2$, y, and $y^2$ are each compared with their corresponding coefficients in Eq. (30), the desired relationships for $r_2$, $p^2$, $\epsilon_2$, and $\eta_2$ are finally obtained.

$$p_2 = \frac{A}{B}$$  Eq. (41)

$$r_2^2 = \frac{1}{B^2} \cdot \left( A + \frac{D^2}{4} + \frac{p_2 E^2}{4} \right)$$  Eq. (42)

$$\varepsilon_2 = \frac{2r_2 B + D}{-2A}$$  Eq. (43)

$$\eta_2 = \frac{E}{-2B}$$  Eq. (44)

Figure 4:
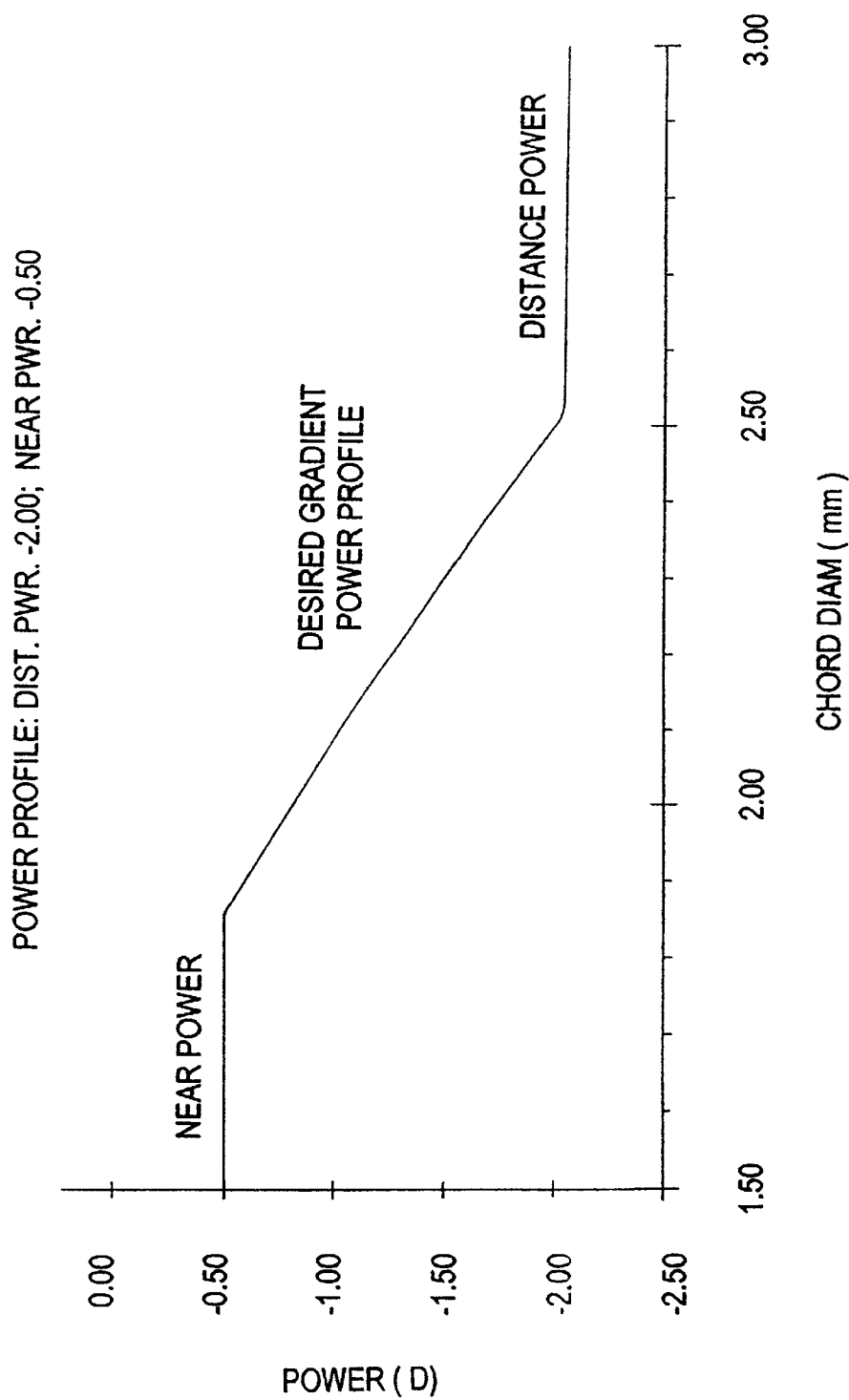
FIG. 4 is a graph illustrating the optical power as a function of chord diameter of a preferred embodiment.

It has been assumed that the apex position of the third zone given by $\epsilon_3$ satisfies only the general requirement for $Z_{13}$ given by Eq. (14). However, it is an object of the present invention that the aspheric second zone provides a useful optical zone in which the gradient power changes monotonically in one direction only. Such a power profile is illustrated in FIG. 4. In FIG. 4 the optical power is plotted as a function of the chord diameter 2y for an example of the preferred embodiment of the present invention. The optical power within the central first zone is essentially constant at the near power value. Within the peripheral third zone the power is essentially constant at the distance power value. Within the second zone the power changes continuously and monotonically from the near value to the distance value. A sufficient condition to produce this desired form of the power profile within the second zone is that $\eta_2 = 0$. Therefore, it is a requirement of the preferred embodiment of the present invention that $\eta_2 = 0$.

From Eq. (44) we have that $\eta_2 = 0$ when E=0. By expanding the determinant in Eq. (40), it may shown that $\eta_2 = E = 0$ when the relationship given below in Eq. (45) is satisfied.

$$(x_1 - x_3) = \frac{(y_1 - \eta_1)^2 - (y_3 - \eta_3)^2}{(y_1 - \eta_1)y_1' - (y_3 - \eta_3)y_3'}$$  Eq. (45)

In fact, Eq. (45) is the desired constraint on $\epsilon_3$. Eq. (46) is an identity which may be rearranged to the form given in Eq. (47). The terms in Eq. (47) may then be evaluated using Eq. (45) and Eq. (7). The result is the condition on $\epsilon_3$ for the third surface (whether or not it is assumed that $\epsilon_1 = 0$) that in conjunction with the continuity requirements makes $\eta_2 = 0$ and that also guarantees that the power profile of the aspheric second zone will have the desired property of the monotonic progression shown in FIG. (4).

$(x_1 - \epsilon_1) - (x_3 - \epsilon_3) = (x_1 - x_3) - (\epsilon_1 - \epsilon_3)$  Eq. (46)

$(\epsilon_1 - \epsilon_3) = (x_1 - x_3) - (x_1 - \epsilon_1) + (x_3 - \epsilon_3)$  Eq. (47)

It is found that departures of the surface from the preferred embodiment that are surprisingly small (about half a micron) can produce undesirable optical effects. Because such small physical departures from the preferred embodiment can produce significant optical effects such as undesirable bumps or dips in the power profile, the manufacturing process must be highly controlled such that the required surface profile is faithfully produced. In prior art lenses where an aspheric surface is created by a polishing or blending process, the process is not controlled sufficiently to permit an analytic description of the resulting surface profile. This low level of control can not reliably satisfy the specific requirements which produce the desired power profile shown in FIG. (4), and hence it is far more probable that the power profiles obtained by polishing or blending have the undesirable effects shown in FIGS. (5) and (6).

The contact lens 10 conforms to the following conditions which results in a lens having the advantages of both a spherical and aspherical lens.

1. When the surface profile of the contact lens 10 is viewed in cross-section (FIG. 3), both the intersections of the intermediate area 14 with the center area 12 and with the outer area 16 are smooth, continuous, and without sharp corners. As an arbitrary point on the surface profile approaches an intersection from either side, the tangent to the curve at that point approaches the exact same value at the actual intersection point. Mathematically, the requirement is that the first derivative (dy/dx or y') of the cross-sectional profile is continuous and in particular that the first derivative is continuous at the intersections between the zones.

In the Cartesian coordinate system and the notation used previously this continuity requirement for the first derivative y' may be summarized as follows at the boundary between the center area 12 and the intermediate area 14.

lim y'=$y_1$' as y→$Z_1$/2 from below lim y'=$y_1$' as y→$Z_1$/2 from above and y'=$y_1$' at y=$Z_1$/2

That is, the first derivative y' has a single and unique value $y_1$' at the boundary between center area 12 and the intermediate area 14 and approaches this single value $y_1$' as y approaches $Z_1$/2 from either side of the boundary between the areas.

Similarly, the first derivative y' has a single and unique value $y_3$' at the boundary between the intermediate area 14 and the outer area 16.

lim y'=$y_3$' as y→$Z_2$/2 from below lim y'=$y_3$' as y→$Z_2$/2 from above and y'=$y_3$' at y=$Z_2$/2

2. When viewed in cross-section the surface profile of the contact lens 10 is either always convex or always concave throughout the optical area. There are no local areas in which the direction of concavity changes sign. Mathematically, this means that there are no points of inflection on the surface profile because the second derivative of the surface profile never changes sign. Equivalently, it means that the first derivative or tangent changes monotonically as an arbitrary point on the surface profile moves across the areas. The surface profile is without sharp corners and is even without rounded corners. The surface profile is smooth and without "bumps" or "waves" which would imply either sharp or rounded corners.

Figure 5:
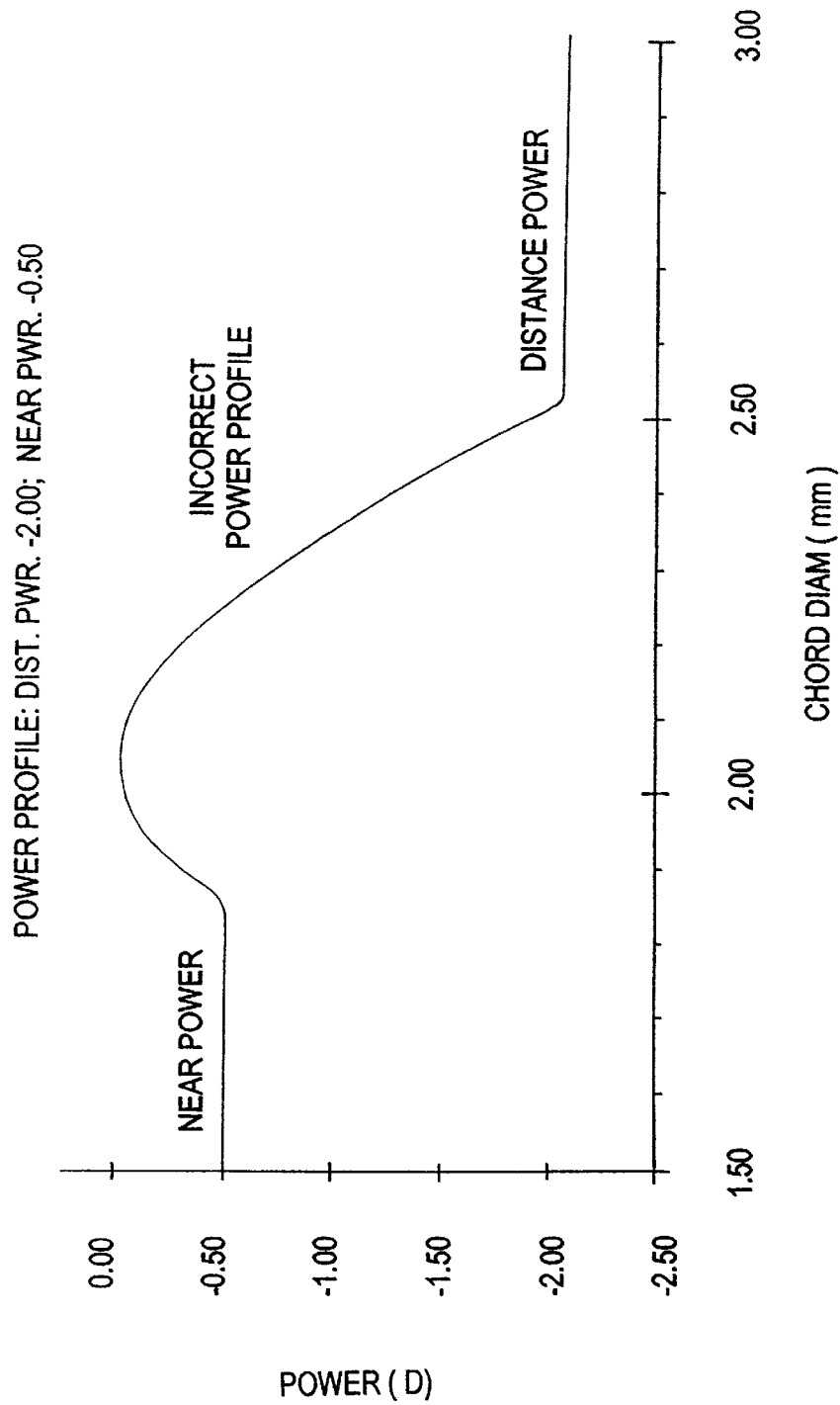
FIG. 5 is a graph illustrating a lens having an incorrect power profile.
Figure 6:
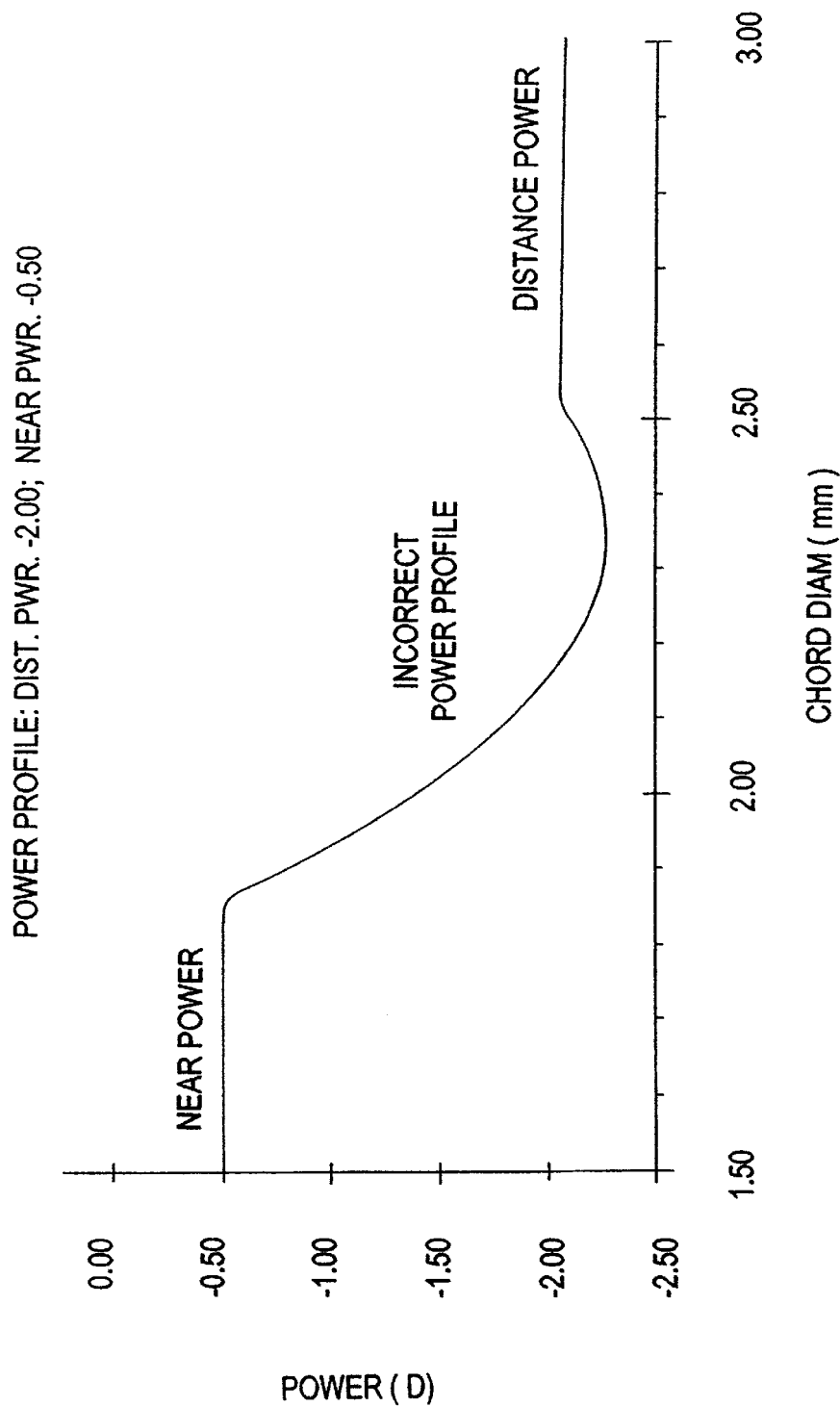
FIG. 6 is a graph illustrating another lens having an incorrect power profile.

3. The aspheric intermediate area 14 is an area of gradient power in which the power changes continuously and monotonically from the power of the center area 12 to the power of the outer area 16. The precise shape of the aspheric surface must be specifically calculated to provide this intended power profile, since very small deviations from the required shape can produce the type of undesired power profiles which are illustrated in FIGS. 5 and 6. By providing such a continuous and monotonically changing power profile, the intermediate aspheric area 14 serves as an optical area of extended depth of focus and also provides useful vision for intermediate viewing distances.

Subject to the above three conditions, the dimensions of the areas must then be computed to maximize the utilization of pupil area for distance, near, and intermediate vision. In this process all of the above three conditions must be satisfied in the present invention. The failure to meet all of the conditions creates the potential for the visual disturbances which are common and pronounced in prior art lenses. These visual disturbances may be induced by edge effects at the boundaries of the component areas and also by the presence of an inappropriate power profile resulting from an aspheric surface which is not well characterized and controlled.

Unlike the conventional concentric zone designs the integration in the present invention of single power areas with a monotonic gradient power area achieves a greater utilization of the pupil area at any moment in time whether the object of regard is at distance, at near, or at intermediate viewing. This maximizes the visual information that is available for objects of regard at all viewing distances. Pupil size dependence is reduced because a greater portion of the pupil is utilized at any time. This is achieved without introducing undesirable edge or bifocal jump effects at the area boundaries since, when properly configured, a seamless transition between the single power areas is provided by the intermediate area 14.

Figure 7:
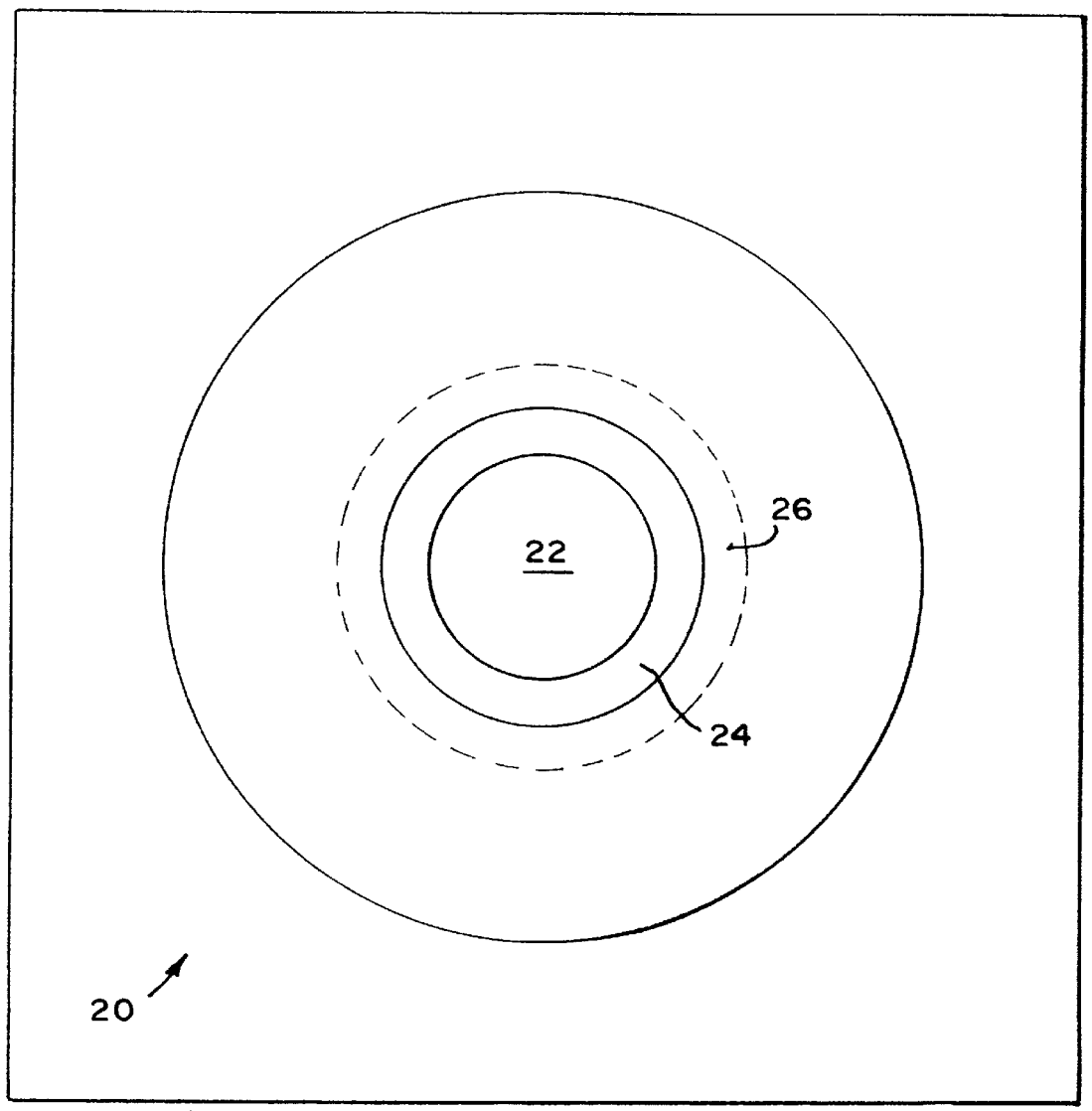
FIG. 7 is a front view of the optical portion of a contact lens constructed in accordance with another preferred embodiment.

In another embodiment of the present invention shown in FIG. 7 the lens is similar to the preferred embodiment of FIG. 1 except that the diameters of the three areas are configured to provide a greater percentage of pupil area for the near optical power. The intermediate area 24 is still computed to satisfy all the conditions listed above for the present invention:

TABLE 6

| Area | Diam | Power | % Area within 3.0 mm pupil | % Area within 3.5 mm pupil | % Area within 4.0 mm pupil | % Area within 4.5 mm pupil | % Area within 5.0 mm pupil |
| --- | --- | --- | --- | --- | --- | --- | --- |
| Area 22 | 2.07 mm | Near | 48% | 35% | 27% | 21% | 17% |
| Area 24 | 2.71 mm | Gradient | 34% | 25% | 19% | 15% | 12% |
| Area 26 | 7.50 mm | Distance | 18% | 40% | 54% | 64% | 71% |

From the above table for this configuration it may be seen that for smaller pupil diameters, the proportion of pupil area devoted to near power approaches the 50% level of prior art lenses.

It is found for the average user, however, that this configuration does not provide the best visual performance over a full range of distance, intermediate, and near viewing conditions. A useful clinical evaluation must include not only objective measures of visual performance such as provided by visual acuity assessment but also subjective ratings of vision quality provided by the subject. The preferred embodiment illustrated in FIG. 1 has improved performance as compared to the embodiment of FIG. 7. This is consistent with the previous finding that the central area with near power should represent less than 50% of the pupil area in order to provide for a full range of viewing distances.

Figure 8:
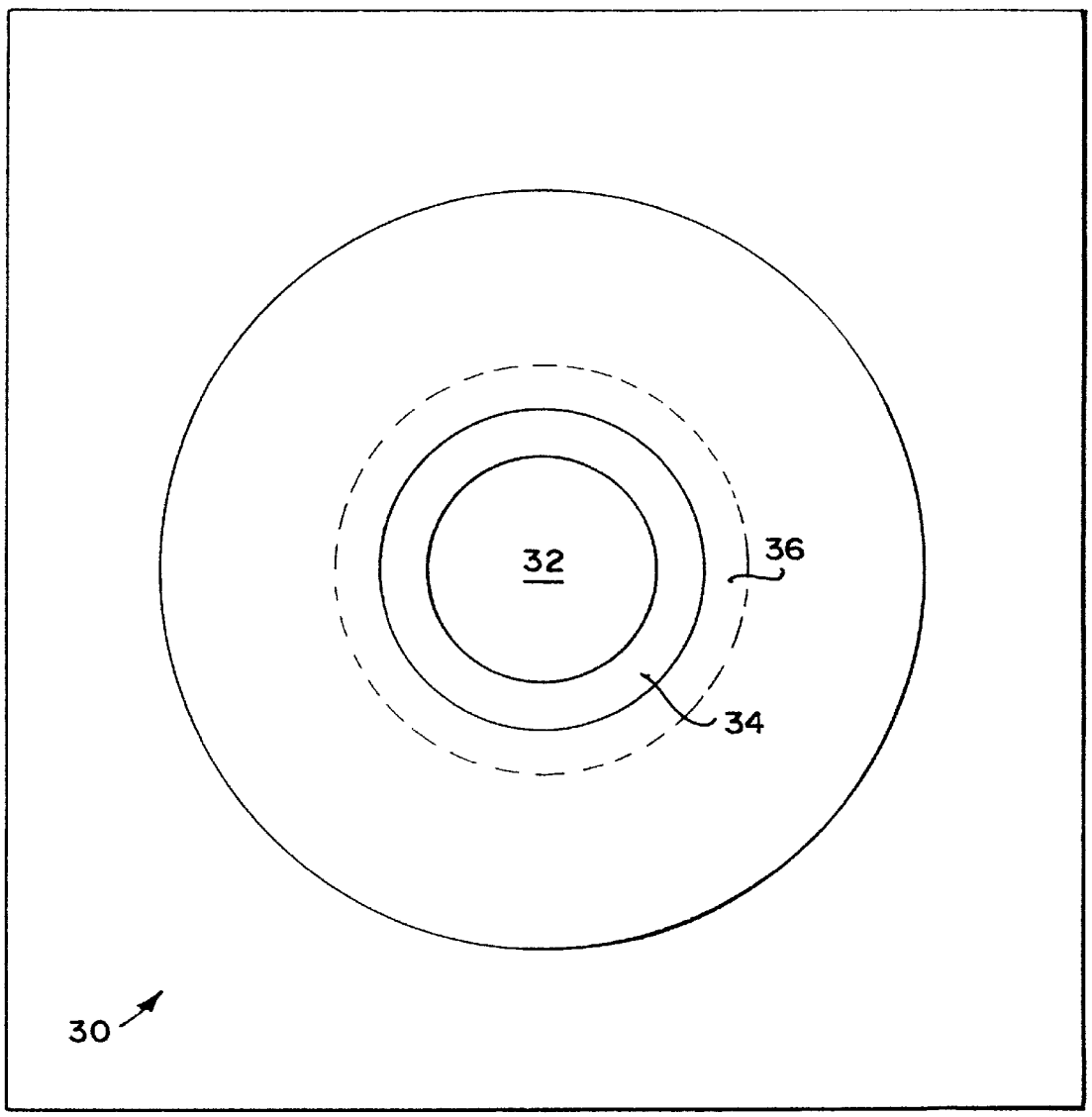
FIG. 8 is a front view of the optical portion of a contact lens constructed in accordance with another preferred embodiment.
Figure 9:
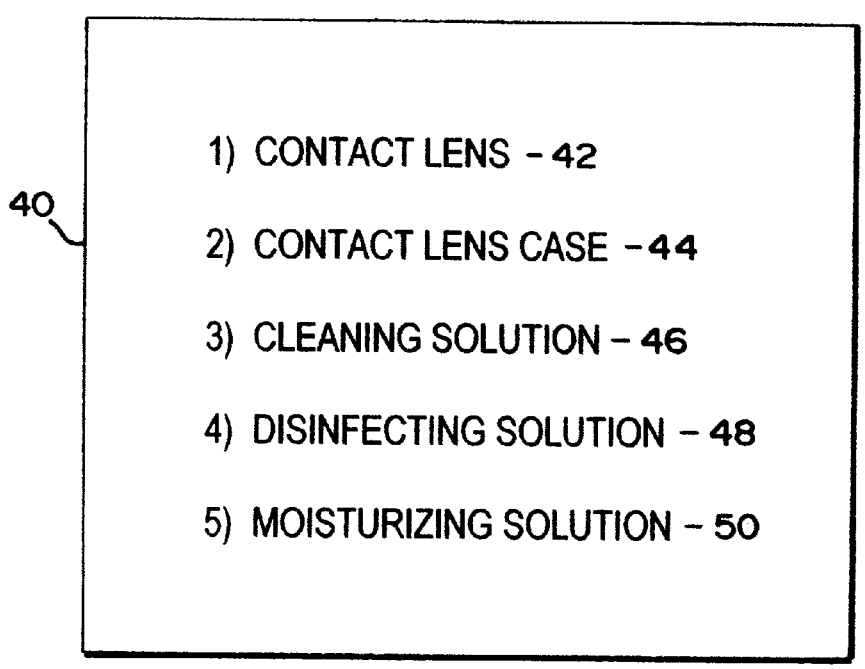
FIG. 9 is a diagram illustrating a kit constructed in accordance with another preferred embodiment.

Another alternate embodiment of the present invention is shown in FIG. 8. The contact lens 30 shown is a distance center embodiment. In the preferred embodiment, the center area 32 is a single power area that provides the desired distance power. The outer area 36 is a single power area that provides the near power. The intermediate area 34 is a gradient power aspheric area that provides a continuous power transition from the center area 32 to the outer area 36. In the embodiment of FIG. 8 the diameters of the different power areas are the same as in FIG. 7 but the order of distance and near powers is reversed:

TABLE 7

| Area | Diam | Power | % Area within 3.0 mm pupil | % Area within 3.5 mm pupil | % Area within 4.0 mm pupil | % Area within 4.5 mm pupil | % Area within 5.0 mm pupil |
|---|---|---|---|---|---|---|---|
| Area 32 | 2.07 mm | Distance | 45% | 35% | 27% | 21% | 17% |
| Area 34 | 2.71 mm | Gradient | 34% | 25% | 19% | 15% | 12% |
| Area 36 | 7.50 mm | Near | 18% | 40% | 54% | 64% | 71% |

The specifications for the individual surface areas for a sample power range are given below where again for convenience an anterior surface configuration is assumed:

Radius Posterior Surface: 8.30 mm
Center Thickness: 0.08 mm
Refractive Index: 1.412
Bifocal Add Power: +1.50 D

TABLE 8

| Distance Power | Central Area 32 $r_1$ | Aspheric Area 34 | | | Outer Area 36 | |
|---|---|---|---|---|---|---|
| | | $r_2$ | $p_2$ | $\epsilon_2$ | $r_3$ | $\epsilon_3$ |
| −5.00 | 9.253 | 9.601 | 8.5612 | 0.0009 | 8.953 | −0.0023 |
| −4.00 | 9.051 | 9.384 | 8.0829 | 0.0009 | 8.764 | −0.0023 |
| −3.00 | 8.857 | 9.177 | 7.6441 | 0.0009 | 8.582 | −0.0023 |
| −2.00 | 8.672 | 8.978 | 7.2409 | 0.0009 | 8.408 | −0.0023 |
| −1.00 | 8.494 | 8.788 | 6.8697 | 0.0009 | 8.241 | −0.0023 |

The power areas of the present invention may be placed on the anterior or the posterior surface of a soft contact lens fabricated from any suitable soft material which is biocompatible with the eye and which can support surfaces of good optical quality. These soft materials include but are not limited to water containing polymers and co-polymers which are collectively known as hydrogels, silicone elastomers with minimal water, and water containing silicone polymers. Examples of some suitable hydrogel materials are polymers and co-polymers of hydroxyethylmethylmethacrylate, ethoxyethylmethacrylate, diacetone acrylamide, glycerylmethacrylate, methylmethacrylate.

The present invention may also be placed on the anterior or the posterior surface of a rigid contact lens from materials such as polymethylmethacrylate, the various silicone acrylate polymers, and fluoroacrylate polymers.

The lens of the present invention may be manufactured by lathing or molding technology. If by lathing, the lathing equipment must be capable of machining general surfaces which comprise spherical and aspherical profiles. One class of lathe with this capability is commonly referred to as a two-axis or X-Y lathe because the position of a cutting tool can be numerically controlled in two independent and orthogonal directions. In the coordinate system described previously the two orthogonal directions are along the x-axis (the direction of sagittal distance) and the y-axis (the direction of chord diameter). Other lathes control the movement of the cutting tool by scaling the movement of a cam follower. The aspheric surface is produced as the cam follower traces out the profile of a cam or template which serves as a master. However, this method first requires a method for generating the cam which will be the master for the desired aspheric surface; hence, these lathes do not have the flexibility of machining a general aspheric surface at will.

The lathing equipment must also provide levels of precision and accuracy which are adequate to ensure that the specific continuity and power profile requirements of the present invention are satisfied. It has been shown previously that small departures on the order of half a micron from the optimum surface can produce the undesirable power profiles illustrated in FIGS. 5 and 6. Precision X-Y lathes are available which provide this required level of control. Therefore, X-Y lathes provide the preferred method of lathing because they combine all the advantages of flexibility, precision, and accuracy.

Another preferred method of manufacturing the present invention is by molding technology. This method first requires the fabrication of a highly accurate master part which must then be faithfully replicated into the final finished product parts. The master part is often machined from a suitable durable metal using an extremely accurate X-Y lathe. The advantage to this method is that the effort of accurately producing the aspheric surface of the present invention may be concentrated in the fabrication of a very high quality metal master.

In the method known as cast molding the metal master is not used to mold the contact lens directly. Rather in a two-step molding process the metal master is used to injection mold many thousands of plastic masters from polypropylene or from some other suitable hard polymer material. The plastic parts are typically used only once to cast mold the final contact lenses before being discarded. The contact lenses are then hydrated in saline solution to their final form.

The design of the appropriate metal masters for this cast molding process requires the following steps:

1. The shrinkage of the injection molded plastic parts must be determined. In the process used to produce examples of the present invention polypropylene is used, wherein the shrinkage is approximately 1–5% depending on the grade of the polypropylene used, the injection molding process conditions, and other factors.
2. The expansion due to hydration of the chosen contact lens polymer material must be determined. In the present process the expansion of the polymer material is found to be approximately 3–11% depending on the formulation of the polymer.
3. In the present process the metal masters are manufactured using a Moore (Bridgeport, Conn.) aspheric generator lathe to achieve the final desired geometry. The metal masters are then used to injection mold the plastic parts from polypropylene for the cast molding of the final contact lenses.

The contact lens 10 can also be manufactured using a process known as wet cast molding. Low molecular weight diluents may be added to cast hydroxyethyl methacrylate (HEMA) mixtures which are displaced during hydration, providing volumetric control during the hydration process. In the ideal wet cast case, there is zero swelling. In many instances, however, a lower amount of diluent is added such that there is some swelling during the hydration process. Lenses were made employing a range of diluent concentrations, with successful results in each case.

The range of diluent concentrations leads to a corresponding range of solids content in the raw monomer mix. In the present process high solids formulations have been found to provide a better lens performance than low solids formulations. However, low solids formulations appear to have certain advantages, e.g., (1) the low solids monomer contains more diluent and compared to the high solids formulation expands less upon polymerization and hydration; (2) the dimensions of the metal masters for the low solids formulations are therefore closer to that of the final contact lens because the expansion factors are less than those of the high solids formulations; (3) the yields of the low solids formulations are higher because there is less variation in the polymer expansion process when the expansion factor is itself low. Accordingly, if low solids formulations could be implemented so as to perform approximately as well as the high solids formulations, they would be preferred.

A wet cast ultraviolet light absorbing HEMA polymer having a diluent concentration of approximately 33% was chosen as a preferred material, similar to the materials described in U.S. Pat. Nos. 4,028,295; 5,637,726; 5,866,635; and 5,729,322, which are hereby incorporated by reference.

The present invention can also be sold as a kit 40. The kit 40 would include a contact lens 42 constructed in accordance with the present invention in a sterile package and a bacteriostatic or a sterile solution. The lens 42 could also be secured in a vial or a blister package and include a storage case 44. The kit 40 could also include at least one of a cleaning solution 46 and a disinfecting solution 48. The cleaning solution 46 could include conventional cleaning solutions. Similarly, the disinfecting solution 48 could include conventional disinfecting agents. The kit 40 could also include a conventional wetting solution 50.

The present invention may also be used with a durable, frequent replacement, or daily disposable contact lens. A made-to-order (MTO) contact lens could also be implemented with the present invention. This made to order contact lens could include any of the following combination: spherical or toric, colored, printed, UV blocking materials lathed, cast molded, injection molded, or molded on the base curve and lathed on the optical multifocal surface as described in U.S. Pat. No. 5,110,278, the disclosure of which is hereby incorporated by reference for the toric case. The present invention may also be implemented with a colored multifocal and a colored toric multifocal contact lens as described in U.S. Pat. No. 4,976,533 (Knapp), U.S. Pat. No. 4,582,402 (Knapp), U.S. Pat. No. 4,704,017 (Knapp), U.S. Pat. NO. 5,414,477 (Jahnke), and U.S. Pat. No. 4,668,240 (Loshaek), as well as U.S. Pat. No. 5,034,166 (Rawlings), U.S. Pat. No. 5,116,112 (Rawlings), and U.S. Pat. No. 5,302,978 (Evans), the disclosures of which are hereby incorporated by reference. More specifically, the present invention may include an area adjacent to the iris of a user that includes a band of dark substantially light-absorbing power as disclosed in U.S. Pat. No. 5,302,978, the disclosure of which is hereby incorporated by reference. In addition, colored lens patterns, pad printing process and mixtures of inks and binders may be used with the lens of the present invention as disclosed in Ser. No. 09/298,141 filed on Apr. 23, 1999, in the names of M. Quinn and B. Atkins, the disclosure of which is hereby incorporated by reference. For example, a pad printing process using a flexible pad depressed against the surface of the lens to deposit a pattern may be used. The ink would include a pigment, enhancing paste and activation solution. Also, a UV blocking material as disclosed in Ser. No. 09/121,071, filed on Jul. 21, 1998, in the name of Hermann Faubl, the disclosure of which is incorporated by reference, may also be implemented with the present invention.

In a lens constructed in accordance with U.S. Pat. Nos. 4,976,533, 4,582,402 or 4,704,017, the colorant would be added to the unhydrated lens, which would then undergo a print cure followed by hydration.

The present invention could also use the invention related to toric lens as described in U.S. Pat. Nos. 5,020,898, 5,062,701 and 4,976,533, the disclosures of which are hereby incorporated by reference. Whether or not a patient is presbyopic, it is desirable to provide the optimum optical correction for the patient's refractive error. Therefore, if there is a significant astigmatic component to the refractive error in a presbyopic patient, it is desirable to use the present invention in a toric contact lens. Such a combination would correct the full refractive error of the patent and also compensate for the loss of near focusing power that occurs in presbyopia. Since in most toric contact lenses the toric surface is placed either on the anterior or the posterior surface, from the point of view of economical manufacturing it is convenient (but not required) to place the bifocal element of the present invention on the surface that is not toric; that is, on the surface opposite to the toric surface. In bitoric contact lenses both the anterior and posterior surfaces are toric, and the bifocal element may be on either surface. Any of the methods for stabilizing a toric lens such as prism ballast and thin zones may be used for stabilizing a bifocal toric combination lens.

Figure 10:
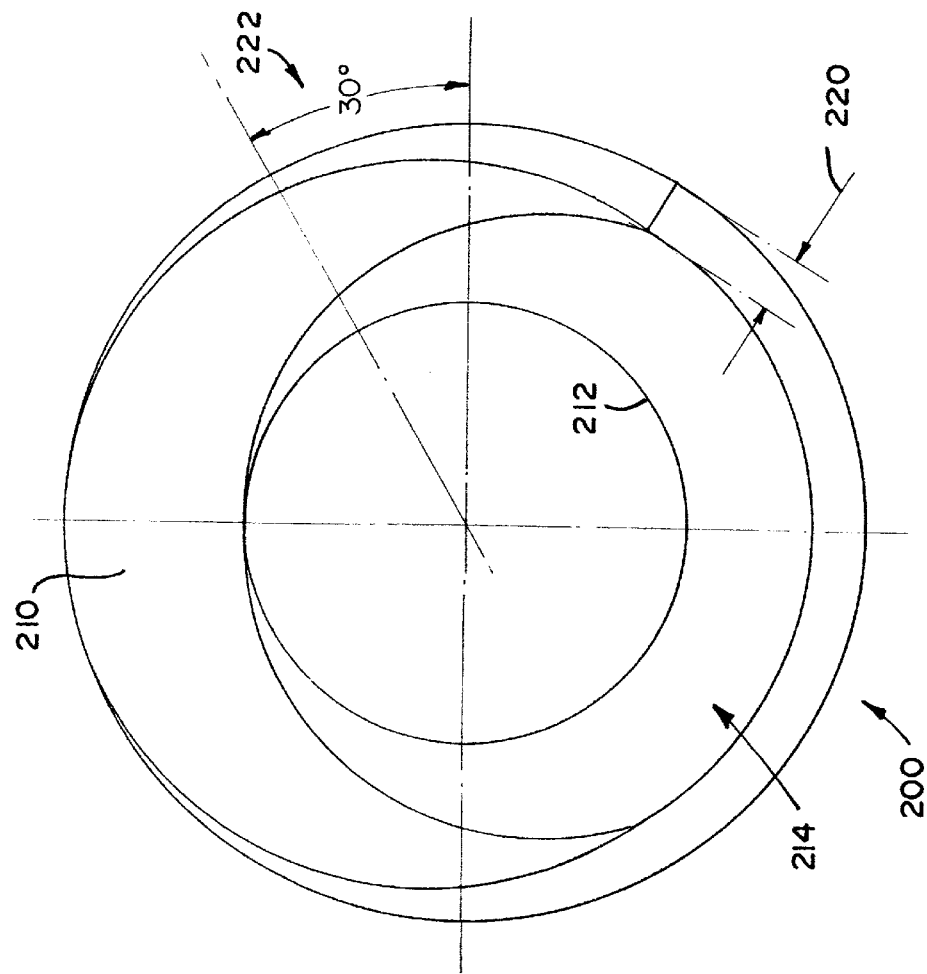
FIG. 10 is a front view of the optical portion of a contact lens constructed in accordance with yet another preferred embodiment.
Figure 11:
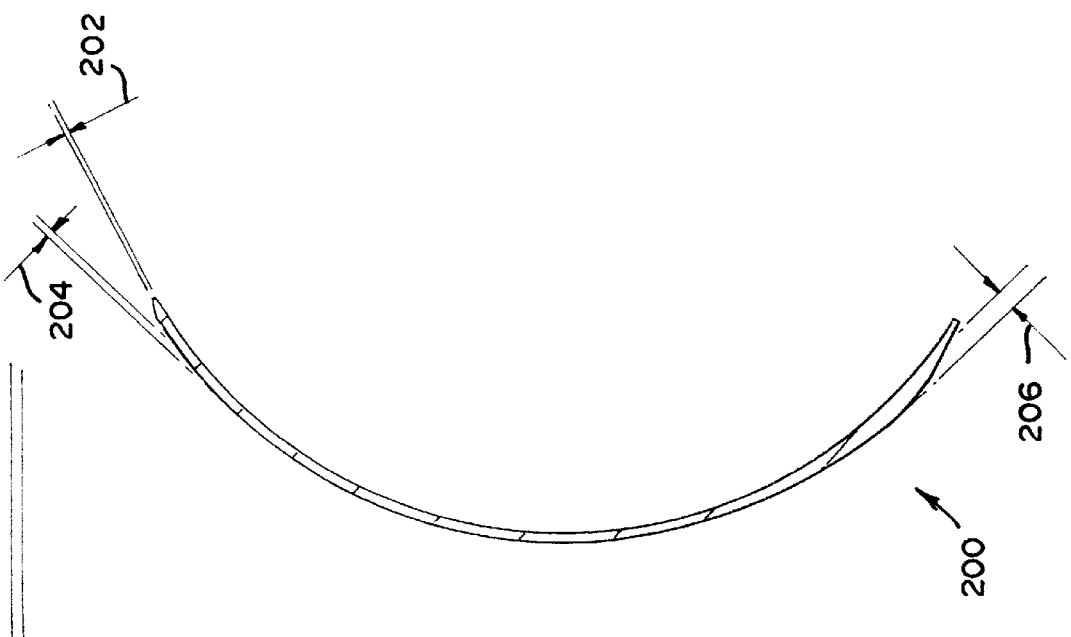
FIG. 11 is a cross-section of the embodiment of FIG. 10.

FIGS. 10 and 11 illustrate a preferred toric lens 200 useful with a toric portion on the front or back surface of the lens of the present invention. The preferred embodiment 200 has an edge lift 202 of 0.030 mm and a peripheral thickness 204 of 0.150 mm. The lens 200 includes a corner thickness 206 of 0.380 mm. With reference to FIG. 11, the upper lenticular portion 210, the optical zone 212, and the carrier 214 are illustrated. In the preferred embodiment, the lens 200 has a trim width 220 of 1.0 mm and a corner angle 222 of 30°. Of course, these dimensions could be modified as recognized by those of ordinary skill in the art.

The present invention could also include a method of using a contact lens constructed in accordance with the present invention. The method would include the step of a user placing the contact lens over a pupil of the user's eye. The contact lens would be constructed in accordance with the present invention.

The present invention also includes a method for prescribing combinations of contact lens configurations each constructed in accordance with the present invention. In many users such a combination of configurations can further enhance the range of visual performance beyond that attained with a single configuration of the present invention. In a method of use known as monovision conventional single vision lenses of different powers are prescribed for the two eyes. Typically, a single vision lens with the distance power prescription is placed on the dominant eye of the user, and a lens with the near power prescription is placed on the non-dominant eye (although in some subjects it can be preferable to reverse this order and to place the lens with the distance power on the non-dominant eye). This method can provide reasonable levels of distance and near vision but with only one eye at a time. Indeed, many users find that the overall level of vision is unacceptable with monovision because the method is disruptive to binocular vision and also because it does not provide for vision at intermediate viewing distances.

Combination prescriptions in the present invention can minimize these disadvantages which limit the success with monovision. In one such combination method a lens in the present invention with a relatively small central area of near power is prescribed one eye. Although near vision is de-emphasized in such a configuration on this eye, the central area is still large enough to provide minimal but useful levels of near vision. On the other hand the distance vision in such a configuration is relatively enhanced. In this same method a lens in the present invention with a relatively large central area of near power is prescribed for the other eye. For the eye with this configuration the near vision is relatively enhanced and the distance vision while not emphasized is still useful. Typically the lens with the relatively small central area of near power is prescribed for the dominant eye, and the lens with the relatively large central area is prescribed for the non-dominant eye, but the reverse order may be preferred in individual cases.

This method of combination prescription has the major advantage of providing a much higher level of binocular vision than is possible with the monovision method because useful levels of both distance and near vision are provided simultaneously to the two eyes. This method also has the advantage of providing binocular intermediate distance vision to both eyes because of the gradient power intermediate areas present in the lenses of each eye. Thus, both of the major limitations to the monovision method are greatly reduced or eliminated by this method of combination prescription in the present invention.

The embodiments described above and shown herein are illustrative and not restrictive. The scope of the invention is indicated by the claims rather than by the foregoing description and attached drawings. The invention may be embodied in other specific forms without departing from the spirit of the invention. For example, additional areas may be incorporated into the present design. In particular, one further embodiment would include an additional aspherical area and an outer spherical area such that the lens included three spherical areas and two aspherical areas. The dimensions of the various areas would have to be sized to fit within the pupil area of a user. Changes that come within the scope of the claims are intended to be embraced herein.

I claim:

1. A multifocal contact lens comprising:
a plurality of areas including a first vision area, a second vision area surrounding the first vision area, and a third vision area surrounding the second vision area, the first vision area having a first substantially single power, the second vision area having a range of powers, the third vision area having a second substantially single power distinct from the first single power, at least one of the first, second and third vision areas having an aspheric surface and the other areas having spherical surfaces wherein the first vision area, the second vision area and the third vision area include intervening transition areas having a single direction of concavity wherein the first vision area has a near correction power and the third vision area has a distance correction power.

2. The lens of claim 1 wherein the first vision area is a center area.

3. The lens of claim 2 wherein the first vision area and third vision area are spherical surfaces and the second vision area is an aspherical surface.

4. The lens of claim 3 wherein the second vision zone has an inner lens diameter between 1.2 mm and 2.1 mm and an outer lens diameter between 2.3 mm and 3.0 mm.

5. The lens of claim 3 wherein the first vision area, the second vision area and the third vision area cover the pupil of a user.

6. The lens of claim 5 wherein the lens includes a UV blocking material.

7. The lens of claim 5 wherein the lens is printed.

8. The lens of claim 5 wherein the lens is pad printed.

9. The lens of claim 8 wherein a flexible pad is depressed against the surface of the lens in order to deposit a pattern.

10. The lens of claim 9 wherein an ink is used including a pigment, an enhancing paste and an activation solution.

11. The lens of claim 5 wherein the area adjacent to an iris of a user includes a band of dark substantially light-absorbing color.

12. The lens of claim 5 wherein the first vision area, the second vision area and the third vision area are located on a first surface of the lens and a toric surface is located on a second surface of the lens.

13. The lens of claim 3 or claim 12 wherein the lens includes a colorant.

14. The lens of claim 12 wherein the first vision area, the second vision area and the third vision area are located on a posterior surface of the lens.

15. The lens of claim 14 wherein at least a portion of the lens is lathed.

16. The lens of claim 5 wherein the lens is cast molded.

17. The lens of claim 5 wherein the lens includes an annular iris color zone.

18. A multifocal contact lens comprising:
a plurality of areas including a first vision area, a second vision area, and a third vision area, the second vision area between the first vision area and the third vision area, the first, second and third vision areas having distinct powers with a monotonic power change and defining a portion of a surface profile of the lens wherein the direction of concavity does not change.

19. The lens of claim 18 wherein the lens is cast molded.

20. The lens of claim 18 wherein the lens is lathed.

21. The lens of claim 20 wherein the lens includes a toric surface portion.

22. The lens of claim 18 wherein the lens includes an annular iris color zone.

23. The lens of claim 18 wherein the second vision area is an optical area having a range of powers for improving vision over a range of distances.

24. The lens of claim 23 wherein the first vision area is a center area and the third vision area is an outer area.

25. The lens of claim 24 wherein the plurality of vision areas are concentric.

26. The lens of claim 25 wherein the lens includes a colorant.

27. The lens of claim 26 wherein the lens includes a green colorant and is translucent.

28. The lens of claim 25 wherein the lens includes an annular iris color zone.

29. The lens of claim 25 wherein the lens includes a UV blocking material.

30. The lens of claim 25 wherein the lens is printed.

31. The lens of claim 30 wherein the lens is pad printed.

32. The lens of claim 30 wherein a flexible pad is depressed against the surface of the lens to deposit a pattern on the surface of the lens.

33. The lens of claim 25 wherein the first vision area, the second vision area and the third vision area are located on a first surface of the lens and a toric surface is located on a second surface of the lens.

34. An ophthalmic kit for use with a multifocal contact lens comprising:
a sterile packaged contact lens in a bacteriostatic or sterile solution, said lens having a plurality of areas including a first vision area, a second area, and a third vision area, the second vision area between the first vision area and the third vision area, the first, second and third vision areas having distinct powers with a monotonic power change and defining a portion of a surface profile of the lens wherein the direction of concavity does not change.

35. The ophthalmic kit of claim 34 wherein the lens is secured in a vial.

36. The ophthalmic kit of claim 34 wherein the lens is secured in a blister package.

37. The ophthalmic kit of claim 34 further comprising a wetting solution.

38. A method of using a multifocal contact lens comprising the steps of: a user placing the contact lens over a pupil of the user's eye, the contact lens having a plurality of areas including a first vision area, a second area, and a third vision area, the second vision area between the first vision area and the third vision area, the first, second and third vision areas having distinct powers with a monotonic power change and defining a portion of a surface profile of the lens wherein the direction of concavity does not change.

39. Multifocal contact lens comprising:
a first spherical zone in the center of the contact lens having a diameter between 1.2 and 2.1 mm, configured to provide vision for near objects;
an aspheric zone surrounding the first spherical zone;
a second spherical zone surrounding the aspheric zone configured to provide vision for distant objects wherein the first spherical zone, the aspheric zone and the second spherical zone include intervening transition areas having a single direction of concavity and a substantially monotonic power change.

40. The contact lens of claim 39 wherein the first spherical zone has a diameter between 1.5 and 1.9 mm.

41. The contact lens of claim 40 wherein the first spherical zone has a diameter of 1.86 mm.

42. The contact lens of claim 40 wherein the first spherical zone has a diameter of 1.83 mm.

43. The contact lens of claim 39 wherein the aspheric zone has an inner lens diameter between 1.2 mm and 2.1 mm, and an outer lens diameter between 2.3 mm and 3.0 mm.

44. The contact lens of claim 39 wherein the second spherical zone has an inner diameter of between 2.3 mm and 3.0 mm, and an outer diameter between 4.0 mm and 8.4 mm.

45. The contact lens of claim 39 wherein the first spherical zone has an area within the range of approximately 1.5 mm$^2$ and 3.5 mm$^2$.

46. The contact lens of claim 39 wherein the second aspherical zone has an area within the range of approximately 1 mm$^2$ and 6 mm$^2$.

47. The contact lens of claim 39 wherein the lens is a phakic intraocular lens.

48. The contact lens of claim 39 wherein the lens is an aphakic intraocular lens.

49. The contact lens of claims 39 wherein the lens is implanted into the posterior chamber of the eye.

50. The contact lens of claims 39 wherein the lens is implanted into the anterior chamber of the eye.

51. The contact lens of claims 39 wherein the lens is implanted into the lens capsule of the eye.

52. The contact lens of claim 39 wherein the lens is implanted into the cornea.

53. The contact lens of claim 39 wherein the lens is an extended wear contact lens, wherein the contact lens may be worn in the eye continuously for a period of 1 to 30 days.

54. The contact lens of claim 39 wherein the lens is a frequent replacement contact lens, wherein the lens is replaced between 1 week and 12 weeks.

55. The contact lens of claim 39 wherein the lens is disposable contact lens.

56. The contact lens of claim 39 wherein the lens is a daily disposable contact lens.

57. The contact lens of claim 39 wherein the lens is a rigid contact lens.

58. The contact lens of claim 39 wherein the lens is a rigid gas permeable contact lens.

59. The contact lens of claim 39 further includes a toric surface portion.

60. The contact lens of claim 39 further includes an ultraviolet light blocking material.

61. The contact lens of claim 60 wherein the ultraviolet light blocking material includes benzotriazole.

62. The contact lens of claim 61 further includes benzphenone.

63. The contact lens of claim 59 further includes a colorant.

64. A method of manufacturing a made-to-order multifocal contact lens comprising the steps of:
measuring at least one of a user's pupil sizes and a required add power for the lens;
manufacturing a multifocal lens having a plurality of vision areas including at least one of sizing the spherical and aspherical areas to suit the needs of the user and providing the lens with an add power corresponding to the required add power of the user, the lens including a first vision area, a second vision area surrounding the first vision area, and a third vision area surrounding the second vision area, the first vision area having a first substantially single power, the second vision area having a range of powers, the third vision area having a second substantially single power distinct from the first single power, at least one of the first, second and third vision areas having an aspheric surface and the other areas having spherical surfaces wherein the first vision area, the second vision area and the third vision area include intervening transition areas having a single direction of concavity and a monotonic power change.

65. The method of claim 64 wherein the lens includes a colorant.

66. The method of claim 64 wherein the lens is printed.

67. The method of claim 66 wherein the lens is pad printed.

68. The method of claim 67 wherein a flexible pad is depressed against the surface of the lens in order to deposit a pattern.

69. The method of claim 68 wherein an ink is used including a pigment, an enhancing paste and an activation solution.

70. The method of claim 64 wherein the lens includes an annular iris color zone.

71. The method of claim 64 wherein the lens includes a UV blocking material.

72. The method of claim 64 wherein the lens includes a toric surface portion.

73. The method of claim 72 wherein the toric surface is located on an anterior surface of the lens and the plurality of vision areas are located on a posterior surface of the lens.

74. The method of claim 73 wherein the toric surface portion is molded and the plurality of vision areas are lathed.

75. The method of claim 64 wherein the lens area adjacent to an iris of a user that includes a dash band of substantially light-absorbing color.

76. The method of claim 64 wherein the lens includes an opaque colorant.

* * * * *